(12) United States Patent
Zergiebel et al.

(10) Patent No.: US 8,506,580 B2
(45) Date of Patent: Aug. 13, 2013

(54) SURGICAL CLIP APPLIER

(75) Inventors: Earl M. Zergiebel, Guilford, CT (US); Kenneth H. Whitfield, New Haven, CT (US); Gregory Sorrentino, Wallingford, CT (US); Kevin Robert Slisz, Old Saybrook, CT (US); Roberto Pedros, Oxford, CT (US)

(73) Assignee: Covidien LP, Mansfield, MA (US)

( * ) Notice: Subject to any disclaimer, the term of this patent is extended or adjusted under 35 U.S.C. 154(b) by 695 days.

(21) Appl. No.: 12/595,318

(22) PCT Filed: Apr. 10, 2008

(86) PCT No.: PCT/US2008/059859
§ 371 (c)(1),
(2), (4) Date: Jan. 21, 2010

(87) PCT Pub. No.: WO2008/127968
PCT Pub. Date: Oct. 23, 2008

(65) Prior Publication Data
US 2010/0137886 A1 Jun. 3, 2010

Related U.S. Application Data

(60) Provisional application No. 60/922,946, filed on Apr. 11, 2007.

(51) Int. Cl.
*A61B 17/10* (2006.01)
(52) U.S. Cl.
USPC .......................................................... 606/143
(58) Field of Classification Search
None
See application file for complete search history.

(56) References Cited

U.S. PATENT DOCUMENTS

| | | |
|---|---|---|
| 3,120,230 A | 2/1964 | Skold |
| 3,638,847 A | 2/1972 | Noiles et al. |
| 4,242,902 A | 1/1981 | Green |

(Continued)

FOREIGN PATENT DOCUMENTS

| | | |
|---|---|---|
| EP | 0 085 931 A2 | 8/1983 |
| EP | 0 324 166 A2 | 7/1989 |

(Continued)

OTHER PUBLICATIONS

European Search Report corresponding to EP 09252053; date of mailing is Dec. 1, 2009; date of completion of Search is Nov. 24, 2009 (3 Pages).

(Continued)

*Primary Examiner* — Julian Woo
*Assistant Examiner* — Son Dang

(57) ABSTRACT

A surgical clip applier is provided including a housing; a pair of handles; a channel assembly extending from the housing; a clip carrier disposed within said channel assembly and defining a channel and a plurality of windows; a wedge plate slidably disposed within said channel assembly and being operatively connected to said handles, said wedge plate including a plurality of apertures formed along a length thereof; a plurality of clips slidably disposed within said channel of said clip carrier; and a clip follower slidably disposed within said channel of said clip carrier at a location proximal of said plurality of clips. The clip follower is configured and adapted for selective engagement with said windows of said clip carrier and said apertures of said wedge plate to distally urge said plurality of clips relative to said clip carrier upon a distal advancement of said wedge plate.

24 Claims, 28 Drawing Sheets

(56) References Cited

U.S. PATENT DOCUMENTS

| | | |
|---|---|---|
| 4,296,751 A | 10/1981 | Blake, III et al. |
| 4,372,316 A | 2/1983 | Blake, III et al. |
| 4,408,603 A | 10/1983 | Blake, III et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A * | 12/1987 | Peters et al. .................. 606/143 |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A * | 9/1991 | Simon et al. .................. 606/143 |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Scjulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |

| | | | | | |
|---|---|---|---|---|---|
| 5,449,365 A | 9/1995 | Green et al. | 5,833,695 A | 11/1998 | Yoon |
| 5,462,555 A | 10/1995 | Bolanos et al. | 5,833,696 A | 11/1998 | Whitfield et al. |
| 5,462,558 A | 10/1995 | Kolesa et al. | 5,833,700 A | 11/1998 | Fogelberg et al. |
| 5,464,416 A | 11/1995 | Steckel | 5,843,097 A | 12/1998 | Mayenberger et al. |
| 5,474,566 A | 12/1995 | Alesi et al. | 5,843,101 A | 12/1998 | Fry |
| 5,474,567 A | 12/1995 | Stefanchik et al. | 5,846,255 A | 12/1998 | Casey |
| 5,474,572 A | 12/1995 | Hayhurst | 5,849,019 A | 12/1998 | Yoon |
| 5,487,746 A | 1/1996 | Yu et al. | 5,858,018 A | 1/1999 | Shipp et al. |
| 5,501,693 A | 3/1996 | Gravener | 5,861,005 A | 1/1999 | Kontos |
| 5,509,920 A | 4/1996 | Phillips et al. | 5,868,759 A | 2/1999 | Peyser et al. |
| 5,514,149 A | 5/1996 | Green et al. | 5,868,761 A | 2/1999 | Nicholas et al. |
| 5,520,701 A | 5/1996 | Lerch | 5,876,410 A | 3/1999 | Petillo |
| 5,522,823 A | 6/1996 | Kuntz et al. | 5,895,394 A | 4/1999 | Kienzle et al. |
| 5,527,318 A | 6/1996 | McGarry | 5,897,565 A | 4/1999 | Foster |
| 5,527,319 A | 6/1996 | Green et al. | 5,904,693 A | 5/1999 | Dicesare et al. |
| 5,527,320 A | 6/1996 | Carruthers et al. | 5,913,862 A | 6/1999 | Ramsey et al. |
| 5,542,949 A | 8/1996 | Yoon | 5,918,791 A | 7/1999 | Sorrentino et al. |
| 5,547,474 A | 8/1996 | Kloeckl et al. | 5,921,996 A | 7/1999 | Sherman |
| 5,569,274 A | 10/1996 | Rapacki et al. | 5,921,997 A | 7/1999 | Fogelberg et al. |
| 5,571,121 A | 11/1996 | Heifetz | 5,928,251 A | 7/1999 | Aranyi et al. |
| 5,575,802 A | 11/1996 | McQuildin et al. | 5,938,667 A | 8/1999 | Peyser et al. |
| 5,582,615 A | 12/1996 | Foshee et al. | 5,951,574 A | 9/1999 | Stefanchik et al. |
| 5,584,840 A | 12/1996 | Ramsey et al. | 5,972,003 A | 10/1999 | Rousseau et al. |
| 5,591,178 A | 1/1997 | Green et al. | 5,976,159 A | 11/1999 | Bolduc et al. |
| 5,593,414 A | 1/1997 | Shipp et al. | 5,993,465 A | 11/1999 | Shipp et al. |
| 5,593,421 A | 1/1997 | Bauer | 6,004,335 A | 12/1999 | Vaitekunas et al. |
| 5,601,573 A | 2/1997 | Fogelberg et al. | 6,017,358 A | 1/2000 | Yoon et al. |
| 5,601,574 A | 2/1997 | Stefanchik et al. | RE36,720 E | 5/2000 | Green et al. |
| 5,607,436 A | 3/1997 | Pratt et al. | 6,059,799 A | 5/2000 | Aranyi et al. |
| 5,618,291 A | 4/1997 | Thompson et al. | 6,099,536 A | 8/2000 | Petillo |
| 5,618,306 A | 4/1997 | Roth et al. | 6,099,537 A | 8/2000 | Sugai et al. |
| 5,620,452 A | 4/1997 | Yoon | 6,139,555 A | 10/2000 | Hart et al. |
| 5,626,585 A | 5/1997 | Mittelstadt et al. | 6,210,418 B1 | 4/2001 | Storz et al. |
| 5,626,586 A | 5/1997 | Pistl et al. | 6,217,590 B1 | 4/2001 | Levinson |
| 5,626,592 A | 5/1997 | Phillips et al. | 6,228,097 B1 | 5/2001 | Levinson et al. |
| RE35,525 E | 6/1997 | Stefanchik et al. | 6,241,740 B1 | 6/2001 | Davis et al. |
| 5,634,930 A | 6/1997 | Thornton et al. | 6,258,105 B1 | 7/2001 | Hart et al. |
| 5,643,291 A | 7/1997 | Pier et al. | 6,261,302 B1 | 7/2001 | Voegele et al. |
| 5,645,551 A | 7/1997 | Green et al. | 6,273,898 B1 | 8/2001 | Kienzle et al. |
| 5,645,553 A | 7/1997 | Kolesa et al. | 6,277,131 B1 | 8/2001 | Kalikow |
| 5,649,937 A | 7/1997 | Bito et al. | 6,306,149 B1 | 10/2001 | Meade |
| 5,653,720 A | 8/1997 | Johnson et al. | 6,318,619 B1 | 11/2001 | Lee |
| 5,662,676 A | 9/1997 | Koninckx | 6,322,571 B1 | 11/2001 | Adams |
| 5,662,679 A | 9/1997 | Voss et al. | 6,350,269 B1 | 2/2002 | Shipp et al. |
| 5,665,097 A | 9/1997 | Baker et al. | 6,352,541 B1 | 3/2002 | Kienzle et al. |
| 5,676,676 A | 10/1997 | Porter | 6,391,035 B1 | 5/2002 | Appleby et al. |
| 5,681,330 A | 10/1997 | Hughett et al. | 6,423,079 B1 | 7/2002 | Blake, III |
| 5,683,405 A | 11/1997 | Yacoubian et al. | 6,428,548 B1 | 8/2002 | Durgin et al. |
| 5,695,502 A | 12/1997 | Pier et al. | 6,440,144 B1 | 8/2002 | Bacher |
| 5,695,505 A | 12/1997 | Yoon | 6,461,363 B1 | 10/2002 | Gadberry et al. |
| 5,697,938 A | 12/1997 | Jensen et al. | 6,464,710 B1 | 10/2002 | Foster |
| 5,700,270 A | 12/1997 | Peyser et al. | 6,494,886 B1 | 12/2002 | Wilk et al. |
| 5,700,271 A | 12/1997 | Whitfield et al. | 6,517,536 B2 | 2/2003 | Hooven et al. |
| 5,702,048 A | 12/1997 | Eberlin | 6,520,972 B2 | 2/2003 | Peters |
| 5,709,706 A | 1/1998 | Kienzle et al. | 6,527,786 B1 | 3/2003 | Davis et al. |
| 5,713,911 A | 2/1998 | Racenet et al. | 6,537,289 B1 | 3/2003 | Kayan et al. |
| 5,713,912 A | 2/1998 | Porter | 6,546,935 B2 | 4/2003 | Hooven |
| 5,720,756 A | 2/1998 | Green et al. | 6,551,333 B2 | 4/2003 | Kuhns et al. |
| 5,722,982 A | 3/1998 | Ferreira et al. | 6,569,171 B2 | 5/2003 | DeGuillebon et al. |
| 5,725,537 A | 3/1998 | Green et al. | 6,579,304 B1 | 6/2003 | Hart et al. |
| 5,725,538 A | 3/1998 | Green et al. | 6,599,298 B1 | 7/2003 | Forster et al. |
| 5,725,542 A | 3/1998 | Yoon | 6,602,252 B2 | 8/2003 | Mollenauer |
| 5,733,295 A | 3/1998 | Back et al. | 6,607,540 B1 | 8/2003 | Shipp |
| 5,755,726 A | 5/1998 | Pratt et al. | 6,613,060 B2 | 9/2003 | Adams et al. |
| 5,766,189 A | 6/1998 | Matsuno | 6,626,916 B1 | 9/2003 | Yeung et al. |
| 5,769,857 A | 6/1998 | Reztzov et al. | 6,626,922 B1 | 9/2003 | Hart et al. |
| 5,772,673 A | 6/1998 | Cuny et al. | 6,648,898 B1 | 11/2003 | Baxter |
| 5,776,146 A | 7/1998 | Sackier et al. | 6,652,538 B2 | 11/2003 | Kayan et al. |
| 5,776,147 A | 7/1998 | Dolendo | 6,652,539 B2 | 11/2003 | Shipp et al. |
| 5,779,718 A | 7/1998 | Green et al. | 6,673,083 B1 | 1/2004 | Kayan et al. |
| 5,779,720 A | 7/1998 | Walder-Utz et al. | 6,676,659 B2 | 1/2004 | Hutchins et al. |
| 5,782,844 A | 7/1998 | Yoon et al. | 6,679,894 B2 | 1/2004 | Damarati |
| 5,788,698 A | 8/1998 | Savornin | RE38,445 E | 2/2004 | Pistl et al. |
| 5,792,149 A | 8/1998 | Sherts et al. | 6,695,854 B1 | 2/2004 | Kayan et al. |
| 5,792,150 A | 8/1998 | Pratt et al. | 6,706,057 B1 | 3/2004 | Bidoia et al. |
| 5,797,922 A | 8/1998 | Hessel et al. | 6,716,226 B2 | 4/2004 | Sixto, Jr. et al. |
| 5,810,853 A | 9/1998 | Yoon | 6,723,109 B2 | 4/2004 | Solingen |
| 5,817,116 A | 10/1998 | Takahashi et al. | 6,743,240 B2 | 6/2004 | Smith et al. |
| 5,827,306 A | 10/1998 | Yoon | 6,773,438 B1 | 8/2004 | Knodel et al. |

| | | | | | | |
|---|---|---|---|---|---|---|
| 6,773,440 | B2 | 8/2004 | Gannoe et al. | 7,297,149 B2 | 11/2007 | Vitali et al. |
| 6,776,783 | B1 | 8/2004 | Frantzen et al. | 7,316,693 B2 | 1/2008 | Viola |
| 6,776,784 | B2 | 8/2004 | Ginn | 7,316,696 B2 | 1/2008 | Wilson, Jr. et al. |
| 6,780,195 | B2 | 8/2004 | Porat | 7,320,692 B1 | 1/2008 | Bender et al. |
| 6,793,663 | B2 | 9/2004 | Kneifel et al. | 7,326,223 B2 | 2/2008 | Wilson, Jr. |
| 6,793,664 | B2 | 9/2004 | Mazzocchi et al. | 7,329,266 B2 | 2/2008 | Royse et al. |
| 6,802,848 | B2 | 10/2004 | Anderson et al. | 7,331,968 B2 | 2/2008 | Arp et al. |
| 6,814,742 | B2 | 11/2004 | Kimura et al. | 7,338,503 B2 | 3/2008 | Rosenberg et al. |
| 6,818,009 | B2 | 11/2004 | Hart et al. | 7,344,544 B2 | 3/2008 | Bender et al. |
| 6,821,273 | B2 | 11/2004 | Mollenauer | 7,357,805 B2 | 4/2008 | Masuda et al. |
| 6,821,284 | B2 | 11/2004 | Sturtz et al. | 7,357,806 B2 | 4/2008 | Rivera et al. |
| 6,824,547 | B2 | 11/2004 | Wilson, Jr. et al. | 7,407,074 B2 | 8/2008 | Ortiz et al. |
| 6,824,548 | B2 | 11/2004 | Smith et al. | 7,419,495 B2 | 9/2008 | Menn et al. |
| 6,835,199 | B2 | 12/2004 | McGuckin, Jr. et al. | 7,431,724 B2 | 10/2008 | Manetakis et al. |
| 6,835,200 | B2 | 12/2004 | Laufer et al. | 7,458,978 B1 | 12/2008 | Bender et al. |
| 6,837,893 | B2 | 1/2005 | Miller | 7,473,258 B2 | 1/2009 | Clauson et al. |
| 6,837,894 | B2 | 1/2005 | Pugsley, Jr. et al. | 7,485,124 B2 | 2/2009 | Kuhns et al. |
| 6,837,895 | B2 | 1/2005 | Mayenberger | 2001/0047178 A1 | 11/2001 | Peters |
| 6,840,945 | B2 | 1/2005 | Manetakis et al. | 2002/0068947 A1 | 6/2002 | Kuhns et al. |
| 6,843,794 | B2 | 1/2005 | Sixto, Jr. et al. | 2002/0082618 A1 | 6/2002 | Shipp et al. |
| 6,849,078 | B2 | 2/2005 | Durgin et al. | 2002/0087169 A1 | 7/2002 | Brock et al. |
| 6,849,079 | B1 | 2/2005 | Blake, III et al. | 2002/0087170 A1 | 7/2002 | Kuhns et al. |
| 6,853,879 | B2 | 2/2005 | Sunaoshi | 2002/0099388 A1 | 7/2002 | Mayenberger |
| 6,869,435 | B2 | 3/2005 | Blake, III | 2002/0120279 A1 | 8/2002 | Deguillebon et al. |
| 6,869,436 | B2 | 3/2005 | Wendlandt | 2002/0128668 A1 | 9/2002 | Manetakis et al. |
| 6,889,116 | B2 | 5/2005 | Jinno | 2002/0177859 A1 | 11/2002 | Monassevitch et al. |
| 6,896,682 | B1 | 5/2005 | McClellan et al. | 2002/0198537 A1 | 12/2002 | Smith et al. |
| 6,905,503 | B2 | 6/2005 | Gifford, III et al. | 2002/0198538 A1 | 12/2002 | Kortenbach et al. |
| 6,911,032 | B2 | 6/2005 | Jugenheimer et al. | 2002/0198539 A1 | 12/2002 | Sixto, Jr. et al. |
| 6,911,033 | B2 | 6/2005 | de Guillebon et al. | 2002/0198540 A1 | 12/2002 | Smith et al. |
| 6,913,607 | B2 | 7/2005 | Ainsworth et al. | 2002/0198541 A1 | 12/2002 | Smith et al. |
| 6,916,327 | B2 | 7/2005 | Northrup, III et al. | 2003/0014060 A1 | 1/2003 | Wilson, Jr. et al. |
| 6,923,818 | B2 | 8/2005 | Muramatsu et al. | 2003/0018345 A1 | 1/2003 | Green |
| 6,939,356 | B2 | 9/2005 | Debbas | 2003/0023249 A1 | 1/2003 | Manetakis |
| 6,942,674 | B2 | 9/2005 | Belef et al. | 2003/0040759 A1 | 2/2003 | de Guillebon et al. |
| 6,942,676 | B2 | 9/2005 | Buelna | 2003/0105476 A1 | 6/2003 | Sancoff et al. |
| 6,945,978 | B1 | 9/2005 | Hyde | 2003/0114867 A1 | 6/2003 | Bolduc et al. |
| 6,945,979 | B2 | 9/2005 | Kortenbach et al. | 2003/0135224 A1 | 7/2003 | Blake, III |
| 6,949,107 | B2 | 9/2005 | McGuckin, Jr. et al. | 2003/0167063 A1 | 9/2003 | Kerr |
| 6,953,465 | B2 | 10/2005 | Dieck et al. | 2003/0225423 A1 | 12/2003 | Huitema |
| 6,955,643 | B2 | 10/2005 | Gellman et al. | 2003/0233105 A1 | 12/2003 | Gayton |
| 6,959,852 | B2 | 11/2005 | Shelton, IV et al. | 2004/0010272 A1 | 1/2004 | Manetakis et al. |
| 6,960,218 | B2 | 11/2005 | Rennich | 2004/0097970 A1 | 5/2004 | Hughett |
| 6,960,221 | B2 | 11/2005 | Ho et al. | 2004/0097971 A1 | 5/2004 | Hughett |
| 6,962,594 | B1 | 11/2005 | Thevenet | 2004/0138681 A1 | 7/2004 | Pier |
| 6,963,792 | B1 | 11/2005 | Green | 2004/0153100 A1 | 8/2004 | Ahlberg et al. |
| 6,964,363 | B2 | 11/2005 | Wales et al. | 2005/0080440 A1 | 4/2005 | Durgin et al. |
| 6,964,668 | B2 | 11/2005 | Modesitt et al. | 2005/0085830 A1 | 4/2005 | Lehman et al. |
| 6,966,875 | B1 | 11/2005 | Longobardi | 2005/0090837 A1 | 4/2005 | Sixto, Jr. et al. |
| 6,966,917 | B1 | 11/2005 | Suyker et al. | 2005/0090838 A1 | 4/2005 | Sixto, Jr. et al. |
| 6,966,919 | B2 | 11/2005 | Sixto, Jr. et al. | 2005/0096670 A1 | 5/2005 | Wellman et al. |
| 6,969,391 | B1 | 11/2005 | Gazzani | 2005/0096671 A1 | 5/2005 | Wellman et al. |
| 6,972,023 | B2 | 12/2005 | Whayne et al. | 2005/0096672 A1 | 5/2005 | Manetakis et al. |
| 6,972,027 | B2 | 12/2005 | Fallin et al. | 2005/0101975 A1 | 5/2005 | Nguyen et al. |
| 6,973,770 | B2 | 12/2005 | Schnipke et al. | 2005/0107807 A1 | 5/2005 | Nakao |
| 6,974,462 | B2 | 12/2005 | Sater | 2005/0107809 A1 | 5/2005 | Litscher et al. |
| 6,974,466 | B2 | 12/2005 | Ahmed et al. | 2005/0107810 A1 | 5/2005 | Morales et al. |
| 6,974,475 | B1 | 12/2005 | Wall | 2005/0107811 A1 | 5/2005 | Starksen et al. |
| 6,981,505 | B2 | 1/2006 | Krause et al. | 2005/0107812 A1 | 5/2005 | Starksen et al. |
| 6,981,628 | B2 | 1/2006 | Wales | 2005/0107871 A1 | 5/2005 | Realyvasquez et al. |
| 6,991,635 | B2 | 1/2006 | Takamoto et al. | 2005/0113847 A1 | 5/2005 | Gadberry et al. |
| 7,052,504 | B2 | 5/2006 | Hughett | 2005/0119671 A1 | 6/2005 | Reydel et al. |
| 7,056,330 | B2 | 6/2006 | Gayton | 2005/0119673 A1 | 6/2005 | Gordon et al. |
| 7,108,703 | B2 | 9/2006 | Danitz et al. | 2005/0119677 A1 | 6/2005 | Shipp |
| 7,144,402 | B2 | 12/2006 | Kuester, III | 2005/0125010 A1 | 6/2005 | Smith et al. |
| 7,175,648 | B2 | 2/2007 | Nakao | 2005/0143767 A1 | 6/2005 | Kimura et al. |
| 7,179,265 | B2 | 2/2007 | Manetakis et al. | 2005/0149063 A1 | 7/2005 | Young et al. |
| 7,207,997 | B2 | 4/2007 | Shipp et al. | 2005/0149064 A1 | 7/2005 | Peterson et al. |
| 7,211,091 | B2 | 5/2007 | Fowler et al. | 2005/0149068 A1 | 7/2005 | Williams et al. |
| 7,211,092 | B2 | 5/2007 | Hughett | 2005/0149069 A1 | 7/2005 | Bertolero et al. |
| 7,214,230 | B2 | 5/2007 | Brock et al. | 2005/0165415 A1 | 7/2005 | Wales |
| 7,214,232 | B2 | 5/2007 | Bowman et al. | 2005/0165418 A1 | 7/2005 | Chan |
| 7,223,271 | B2 | 5/2007 | Muramatsu et al. | 2005/0171560 A1 | 8/2005 | Hughett |
| 7,223,272 | B2 | 5/2007 | Francese et al. | 2005/0177176 A1 | 8/2005 | Gerbi et al. |
| 7,232,445 | B2 | 6/2007 | Kortenbach et al. | 2005/0177177 A1 | 8/2005 | Viola |
| 7,261,724 | B2 | 8/2007 | Molitor et al. | 2005/0203547 A1 | 9/2005 | Weller et al. |
| 7,261,725 | B2 | 8/2007 | Binmoeller | 2005/0203548 A1 | 9/2005 | Weller et al. |
| 7,264,625 | B1 | 9/2007 | Buncke | 2005/0216036 A1 | 9/2005 | Nakao |
| 7,288,098 | B2 | 10/2007 | Huitema et al. | 2005/0216056 A1 | 9/2005 | Valdevit et al. |

| | | | | | | |
|---|---|---|---|---|---|---|
| 2005/0222588 A1 | 10/2005 | Vandenbroek et al. | | 2007/0123916 A1 | 5/2007 | Maier et al. |
| 2005/0222590 A1 | 10/2005 | Gadberry et al. | | 2007/0142848 A1 | 6/2007 | Ainsworth et al. |
| 2005/0222665 A1 | 10/2005 | Aranyi | | 2007/0142851 A1 | 6/2007 | Sixto, Jr. et al. |
| 2005/0228411 A1 | 10/2005 | Manzo | | 2007/0149988 A1 | 6/2007 | Michler et al. |
| 2005/0228416 A1 | 10/2005 | Burbank et al. | | 2007/0149989 A1 | 6/2007 | Santili et al. |
| 2005/0234478 A1 | 10/2005 | Wixey et al. | | 2007/0162060 A1 | 7/2007 | Wild |
| 2005/0251183 A1 | 11/2005 | Buckman et al. | | 2007/0185504 A1 | 8/2007 | Manetakis et al. |
| 2005/0251184 A1 | 11/2005 | Anderson | | 2007/0191868 A1 | 8/2007 | Theroux et al. |
| 2005/0256529 A1 | 11/2005 | Yawata et al. | | 2007/0213747 A1 | 9/2007 | Monassevitch et al. |
| 2005/0267495 A1 | 12/2005 | Ginn et al. | | 2007/0250080 A1 | 10/2007 | Jones et al. |
| 2005/0273122 A1 | 12/2005 | Theroux et al. | | 2007/0265640 A1 | 11/2007 | Kortenbach et al. |
| 2005/0277951 A1 | 12/2005 | Smith et al. | | 2007/0276417 A1 | 11/2007 | Mendes, Jr. et al. |
| 2005/0277952 A1 | 12/2005 | Arp et al. | | 2007/0282355 A1 | 12/2007 | Brown et al. |
| 2005/0277953 A1 | 12/2005 | Francese et al. | | 2007/0293875 A1 | 12/2007 | Soetikno et al. |
| 2005/0277954 A1 | 12/2005 | Smith et al. | | 2008/0004636 A1 | 1/2008 | Walberg et al. |
| 2005/0277955 A1 | 12/2005 | Palmer et al. | | 2008/0004637 A1 | 1/2008 | Klassen et al. |
| 2005/0277956 A1 | 12/2005 | Francese et al. | | 2008/0004639 A1 | 1/2008 | Huitema et al. |
| 2005/0277958 A1 | 12/2005 | Levinson | | 2008/0015615 A1 | 1/2008 | Molitor et al. |
| 2005/0288689 A1 | 12/2005 | Kammerer et al. | | 2008/0027465 A1 | 1/2008 | Vitali et al. |
| 2005/0288690 A1 | 12/2005 | Bourque et al. | | 2008/0027466 A1 | 1/2008 | Vitali et al. |
| 2006/0004388 A1 | 1/2006 | Whayne et al. | | 2008/0045978 A1 | 2/2008 | Kuhns et al. |
| 2006/0004390 A1 | 1/2006 | Rosenberg et al. | | 2008/0045981 A1 | 2/2008 | Margolin et al. |
| 2006/0009789 A1 | 1/2006 | Gambale et al. | | 2008/0051808 A1 | 2/2008 | Rivera et al. |
| 2006/0009790 A1 | 1/2006 | Blake, III et al. | | 2008/0065118 A1 | 3/2008 | Damarati |
| 2006/0009792 A1 | 1/2006 | Baker et al. | | 2008/0065119 A1 | 3/2008 | Viola |
| 2006/0020270 A1 | 1/2006 | Jabba et al. | | 2008/0114377 A1 | 5/2008 | Shibata et al. |
| 2006/0020271 A1 | 1/2006 | Stewart et al. | | 2008/0114378 A1 | 5/2008 | Matsushita |
| 2006/0047305 A1 | 3/2006 | Ortiz et al. | | 2008/0125796 A1 | 5/2008 | Graham |
| 2006/0047306 A1 | 3/2006 | Ortiz et al. | | 2008/0132915 A1 | 6/2008 | Buckman et al. |
| 2006/0064117 A1 | 3/2006 | Aranyi et al. | | 2008/0140089 A1 | 6/2008 | Kogiso et al. |
| 2006/0079912 A1 | 4/2006 | Whitfield et al. | | 2008/0140090 A1 | 6/2008 | Aranyi et al. |
| 2006/0079913 A1 | 4/2006 | Whitfield et al. | | 2008/0147092 A1 | 6/2008 | Rogge et al. |
| 2006/0085015 A1 | 4/2006 | Whitfield et al. | | 2008/0147093 A1 | 6/2008 | Roskopf et al. |
| 2006/0100649 A1 | 5/2006 | Hart | | 2008/0154287 A1 | 6/2008 | Rosenberg et al. |
| 2006/0111731 A1 | 5/2006 | Manzo | | 2008/0167665 A1 | 7/2008 | Arp et al. |
| 2006/0129170 A1 | 6/2006 | Royce et al. | | 2008/0188872 A1 | 8/2008 | Duff |
| 2006/0163312 A1 | 7/2006 | Viola et al. | | 2008/0207995 A1 | 8/2008 | Kortenbach et al. |
| 2006/0173470 A1 | 8/2006 | Oray et al. | | 2008/0208217 A1 | 8/2008 | Adams |
| 2006/0178683 A1 | 8/2006 | Shimoji et al. | | 2008/0228199 A1 | 9/2008 | Cropper et al. |
| 2006/0184182 A1 | 8/2006 | Aranyi et al. | | 2008/0228202 A1 | 9/2008 | Cropper et al. |
| 2006/0190013 A1 | 8/2006 | Menn | | 2008/0243143 A1 | 10/2008 | Kuhns et al. |
| 2006/0195125 A1 | 8/2006 | Sakakine et al. | | 2008/0243145 A1 | 10/2008 | Whitfield et al. |
| 2006/0200179 A1 | 9/2006 | Barker et al. | | 2008/0255589 A1 | 10/2008 | Blakeney et al. |
| 2006/0217749 A1 | 9/2006 | Wilson, Jr. et al. | | 2008/0294178 A1 | 11/2008 | Kortenbach et al. |
| 2006/0224170 A1 | 10/2006 | Duff | | 2008/0306491 A1 | 12/2008 | Cohen et al. |
| 2006/0235437 A1 | 10/2006 | Vitali et al. | | 2008/0306492 A1 | 12/2008 | Shibata et al. |
| 2006/0235438 A1 | 10/2006 | Huitema et al. | | 2008/0306493 A1 | 12/2008 | Shibata et al. |
| 2006/0235439 A1 | 10/2006 | Molitor et al. | | 2008/0312665 A1 | 12/2008 | Shibata et al. |
| 2006/0235440 A1 | 10/2006 | Huitema et al. | | 2008/0312666 A1 | 12/2008 | Ellingwood et al. |
| 2006/0235441 A1 | 10/2006 | Huitema et al. | | 2008/0312670 A1 | 12/2008 | Lutze et al. |
| 2006/0235442 A1 | 10/2006 | Huitema | | 2008/0319456 A1 | 12/2008 | Hart |
| 2006/0235443 A1 | 10/2006 | Huitema et al. | | 2010/0274262 A1 | 10/2010 | Schulz et al. |
| 2006/0235444 A1 | 10/2006 | Huitema et al. | | | | |
| 2006/0259045 A1 | 11/2006 | Damarati | | | | |
| 2006/0259049 A1 | 11/2006 | Harada et al. | | | | |

FOREIGN PATENT DOCUMENTS

| | | |
|---|---|---|
| EP | 0 392 750 A1 | 10/1990 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0 755 655 A | 1/1997 |
| EP | 0 769 274 A1 | 4/1997 |
| EP | 0 769 275 | 4/1997 |
| EP | 0 834 286 | 4/1998 |
| EP | 1 317 906 | 6/2003 |
| EP | 1 609 427 A1 | 12/2005 |
| EP | 1 712 191 A2 | 10/2006 |
| EP | 1712190 A2 | 10/2006 |
| EP | 1 813 199 A1 | 8/2007 |
| EP | 1 908 423 A | 4/2008 |
| EP | 1 908 423 A2 | 4/2008 |
| EP | 1 913 881 A1 | 4/2008 |
| EP | 2 229 895 A1 | 9/2010 |
| JP | 2003 033361 A | 2/2003 |
| WO | WO 2005/091457 | 9/2005 |
| WO | WO 2006/042076 | 4/2006 |
| WO | WO 2006/042084 | 4/2006 |
| WO | WO 2006/042110 | 4/2006 |
| WO | WO 2008/118928 A2 | 10/2008 |
| WO | WO 2008/127968 A | 10/2008 |

2006/0264987 A1 11/2006 Sgro
2006/0271072 A1 11/2006 Hummel et al.
2007/0016228 A1 1/2007 Salas
2007/0021761 A1 1/2007 Phillips
2007/0023476 A1 2/2007 Whitman et al.
2007/0023477 A1 2/2007 Whitman et al.
2007/0027458 A1 2/2007 Sixto, Jr. et al.
2007/0034669 A1 2/2007 De La Torre et al.
2007/0038233 A1 2/2007 Martinez et al.
2007/0049947 A1 3/2007 Menn et al.
2007/0049948 A1 3/2007 Menn et al.
2007/0049949 A1 3/2007 Manetakis
2007/0049950 A1 3/2007 Theroux et al.
2007/0049951 A1 3/2007 Menn
2007/0049953 A2 3/2007 Shimoji et al.
2007/0073314 A1 3/2007 Gadberry et al.
2007/0083218 A1 4/2007 Morris
2007/0093856 A1 4/2007 Whitfield
2007/0106314 A1 5/2007 Dunn
2007/0112365 A1 5/2007 Hilal et al.
2007/0118155 A1 5/2007 Goldfarb et al.
2007/0118161 A1 5/2007 Kennedy et al.
2007/0118163 A1 5/2007 Boudreaux et al.
2007/0118174 A1 5/2007 Chu

OTHER PUBLICATIONS

European Search Report corresponding to European Application No. EP 05 80 2686.5, completed Jan. 9, 2012; mailed Jan. 18, 2012; (3 Pages).
The extended European Search Report corresponding to European Application No. EP 12 15 1313.9, completed Mar. 20, 2012 and mailed Apr. 12, 2012; (5 Pages).
The extended European Search Report corresponding to European Application No. EP 12 16 1291.5, completed Apr. 24, 2012 and mailed May 4, 2012; (5 Pages).
Extended European Search Report corresponding to EP 09252056.8, date of mailing is Feb. 5, 2010; date of completion of Search is Jan. 8, 2010 (3 Pages).
Extended European Search Report corresponding to EP 10250497.4, date of mailing is May 12, 2010; date of completion of Search is May 4, 2010 (6 Pages).
European Search Report corresponding to EP 05810218.7, mailed on May 20, 2011; completed on Apr. 18, 2011; 3 pages.
European Search Report corresponding to EP 05807612.6, mailed on May 20, 2011; completed on May 2, 2011; 3 pages.
Extended European Search Report corresponding to EP 10251737.2, mailed on May 20, 2011; completed on May 9, 2011; 4 pages.
The extended European Search Report corresponding to European Application No. EP 11250214.1, completed May 25, 2011; mailed Jun. 1, 2011; (3 Pages).
International Search Report for application EP 07 25 3905 dated Feb. 7, 2008.
International Search Report from European Application No. EP 07 25 3807 mailed Aug. 1, 2008.
International Search Report from PCT Application No. PCT/US08/58185 dated Sep. 9, 2008.
International Search Report from PCT Application No. PCT/US08/59859 dated Sep. 18, 2008.
The extended European Search Report from Application No. EP 07 25 3807 Nov. 26, 2008.
European Search Report corresponding to EP 09252049; date of mailing is Jan. 12, 2010; date of completion of Search is Dec. 11, 2009 (3 Pages).
European Search Report corresponding to EP 09252051; date of mailing is Jan. 28, 2010; date of completion of Search is Dec. 21, 2009 (3 Pages).
European Search Report corresponding to EP 09252050; date of mailing is Jan. 21, 2010; date of completion of Search is Dec. 23, 2009 (3 Pages).
European Search Report corresponding to EP 09252054; date of mailing is Jan. 22, 2010; date of completion of Search is Jan. 7, 2010 (3 Pages).
Extended European Search Report corresponding to EP 10252079.8, date of mailing is Mar. 17, 2011; date of completion of Search is Mar. 8, 2011 (3 Pages).
European Search Report for corresponding EP08745461 date of mailing is Jun. 5, 2012 (9 pgs).
The extended European Search Report corresponding to European Application No. EP 12 16 2288.0, completed Jun. 4, 2012 and mailed Jul. 7, 2012; (6 Pages).
The extended European Search Report corresponding to European Application No. EP 12 16 5891.8, completed Jun. 12, 2012 and mailed Jun. 20, 2012; (6 Pages).
The extended European Search Report corresponding to European Application No. EP 12 16 4955.2, completed Aug. 23, 2012 and mailed Sep. 4, 2012; (5 Pages).
The extended European Search Report corresponding to European Application No. EP 12 18 6401.1, completed Nov. 22, 2012 and mailed Nov. 30, 2012; (7 Pages).
The extended European Search Report corresponding to European Application No. EP 12 18 6448.2, completed Nov. 28, 2012 and mailed Dec. 10, 2012; (6 Pages).
The extended European Search Report corresponding to European Application No. EP 12 19 1706.6, completed Dec. 19, 2012 and mailed Jan. 8, 2013; (6 Pages).
The extended European Search Report corresponding to European Application No. EP 11 25 0754.6, completed Oct. 22, 2012 and mailed Oct. 31, 2012; (6 Pages).

* cited by examiner

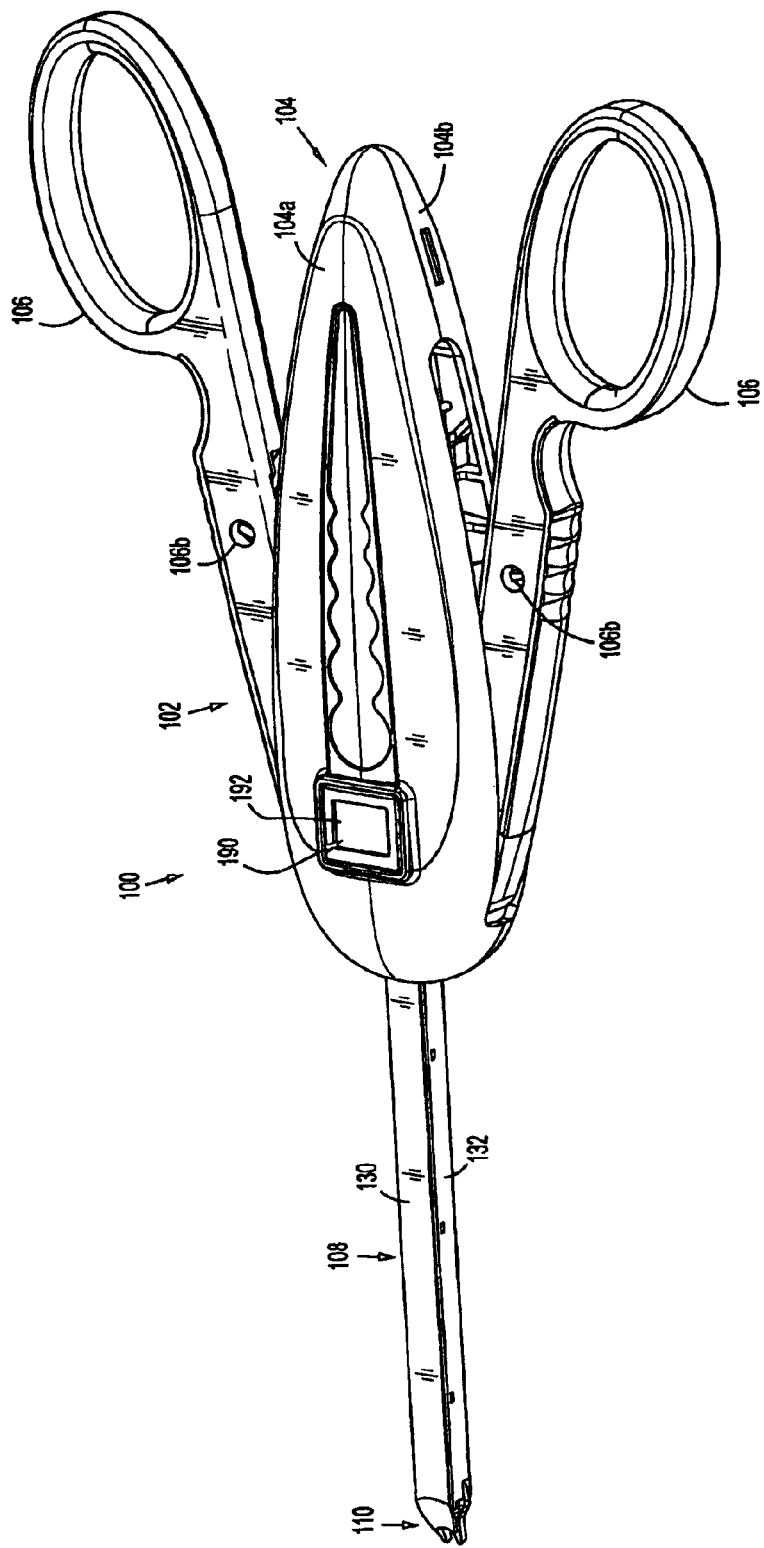

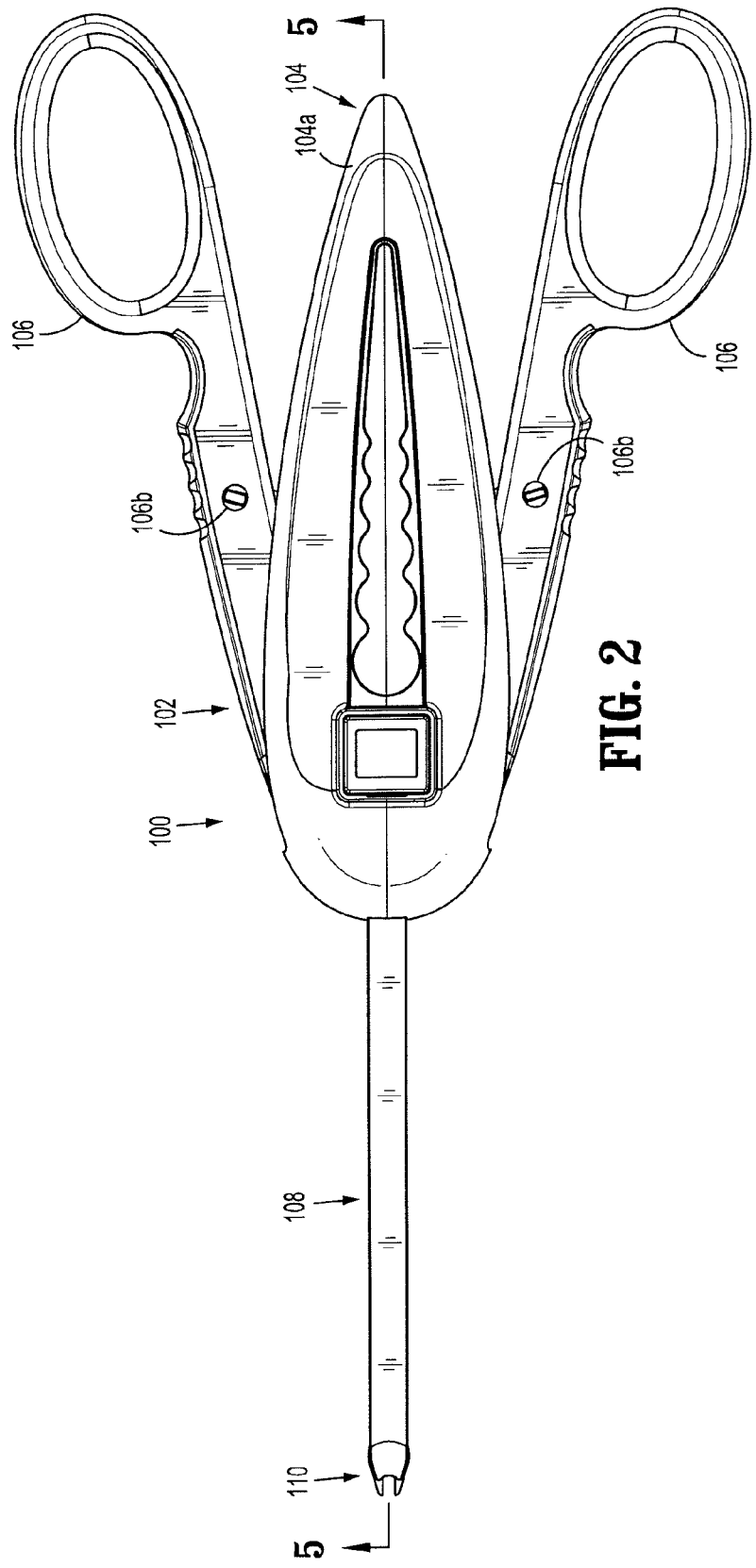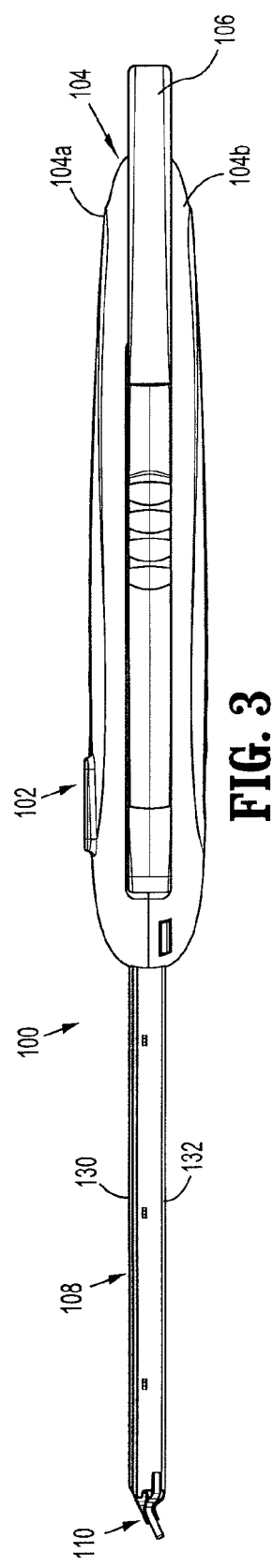

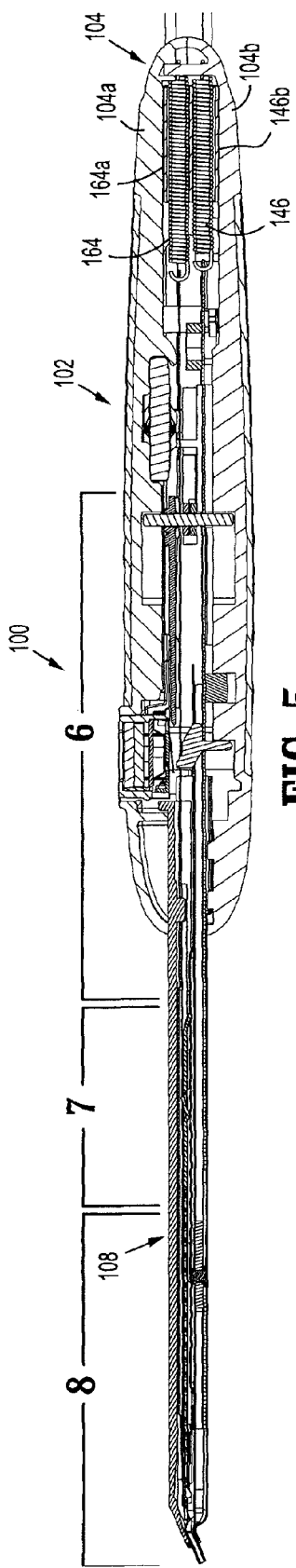
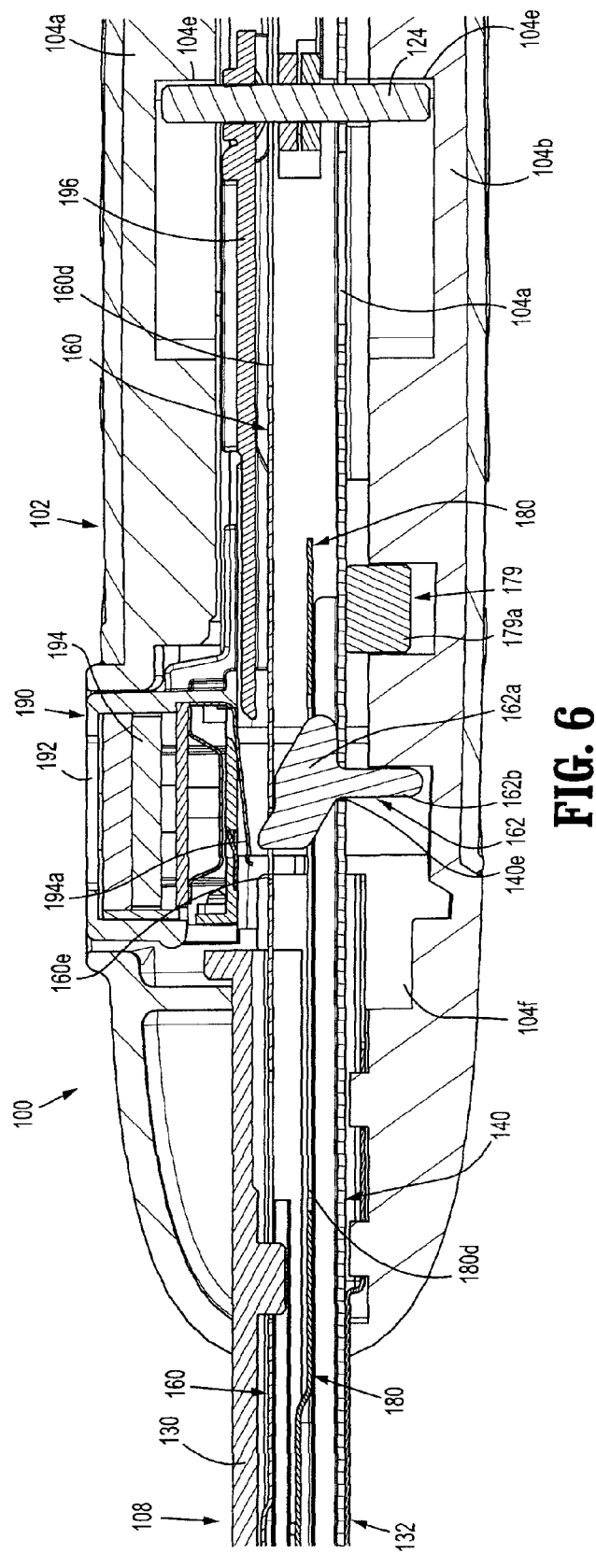
FIG. 5
FIG. 6

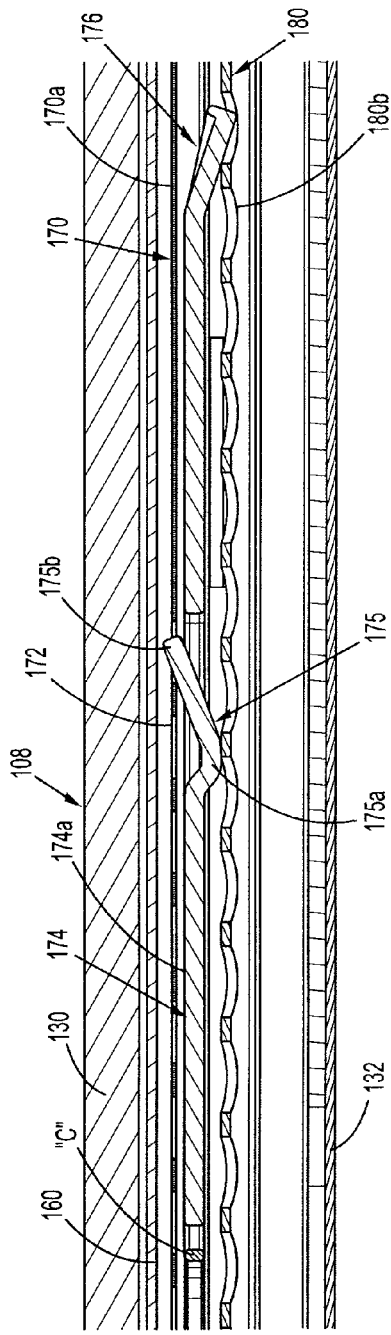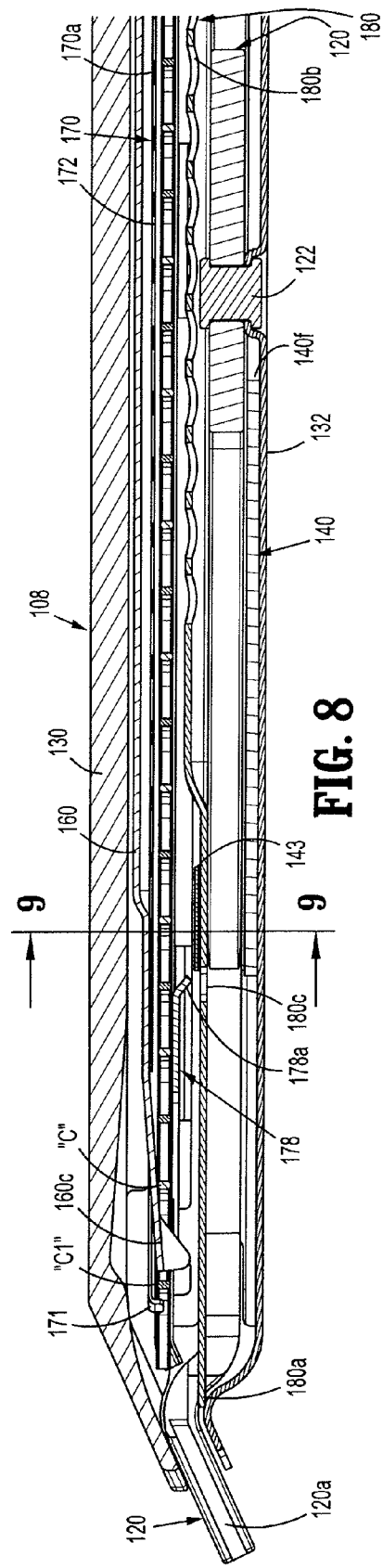
FIG. 7
FIG. 8

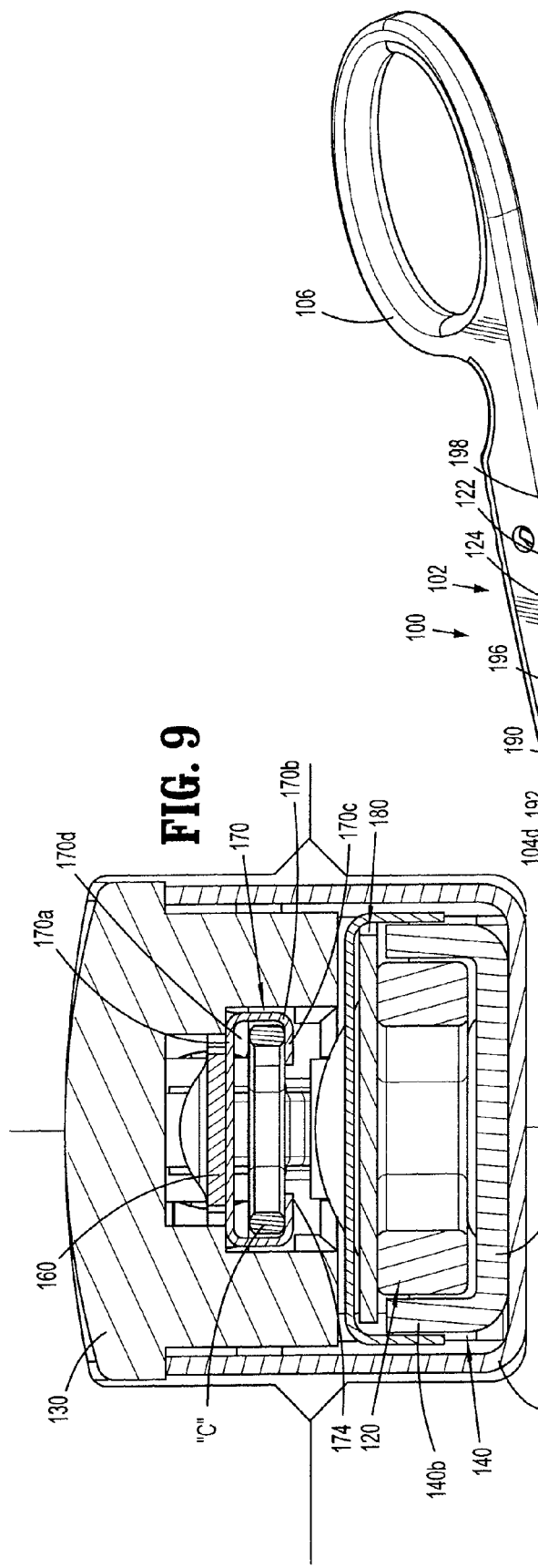
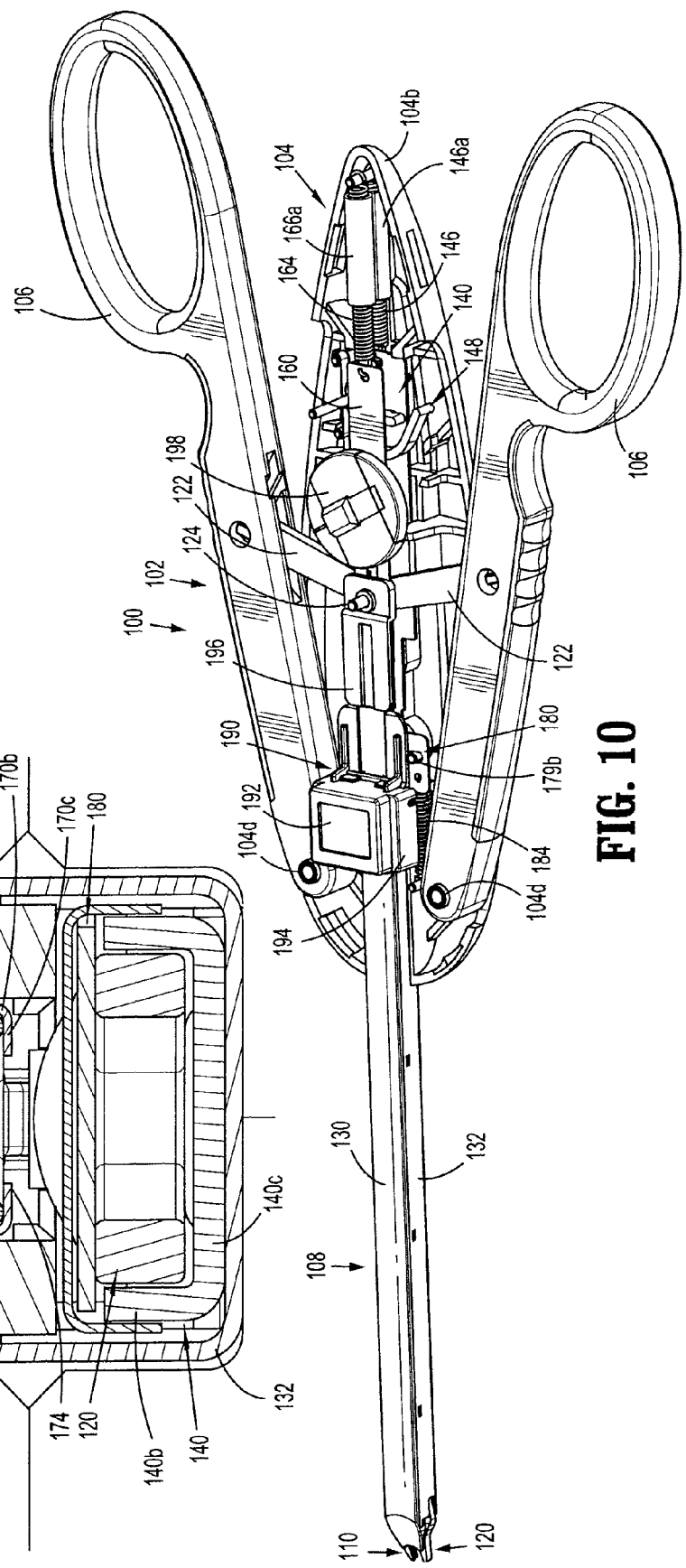

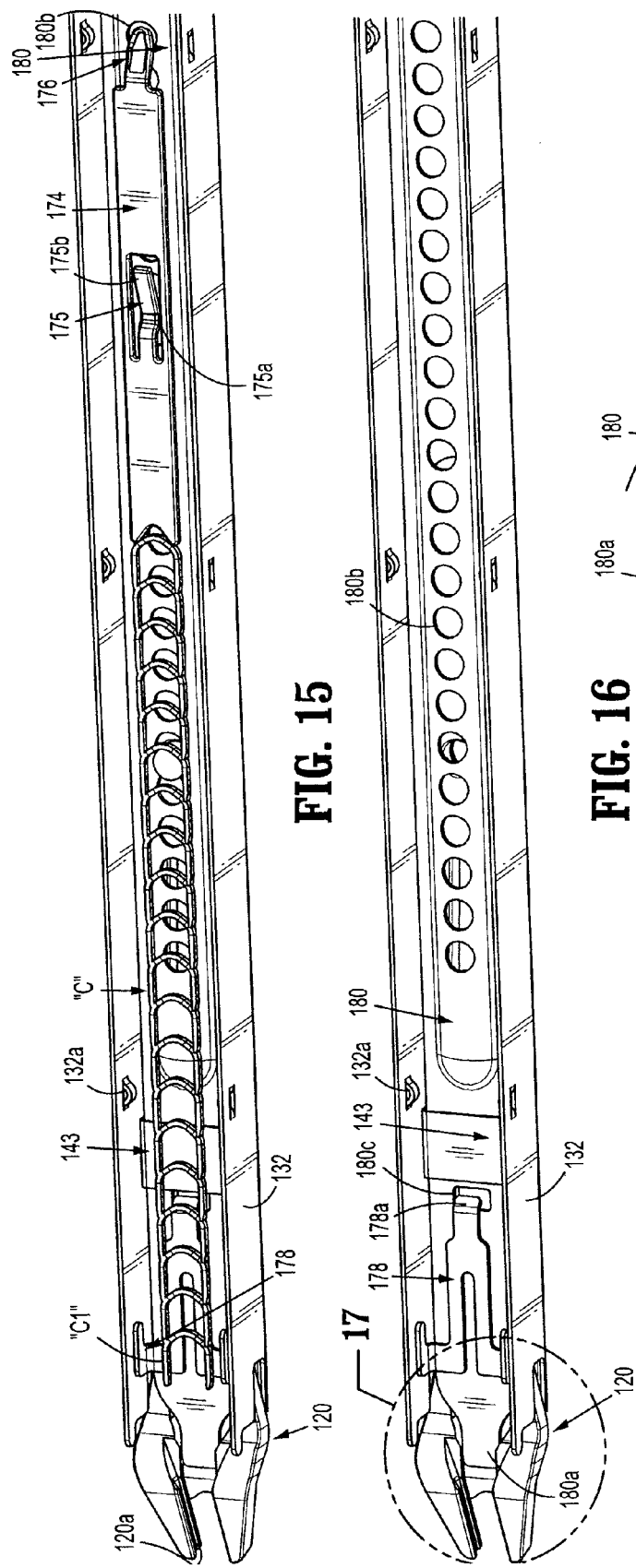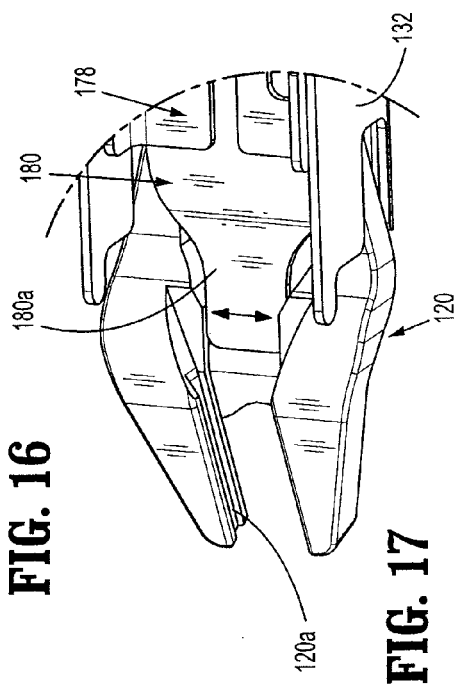
FIG. 15
FIG. 16
FIG. 17

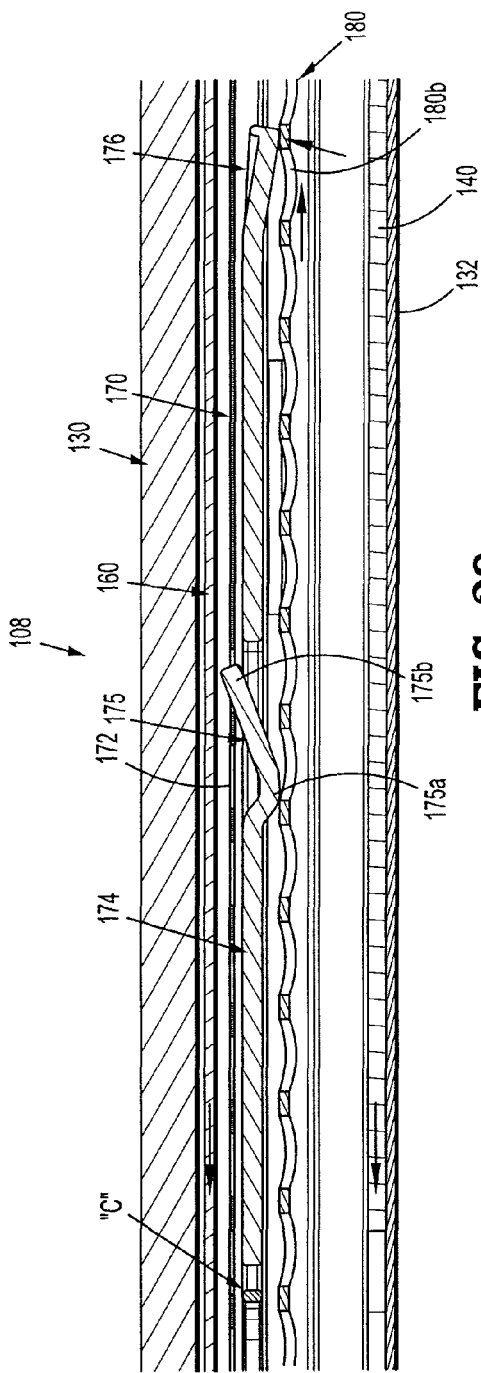
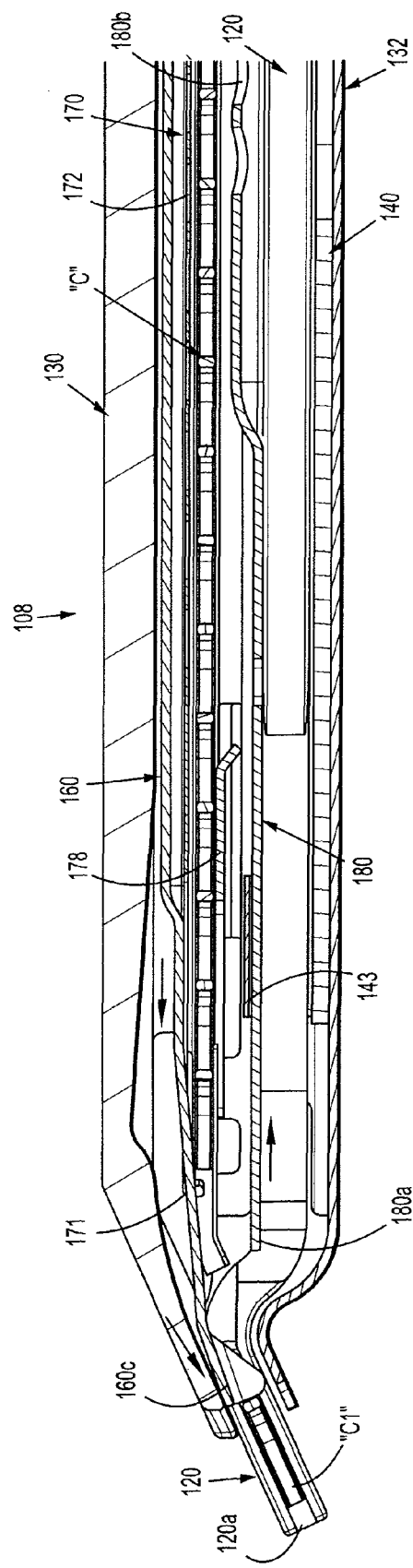

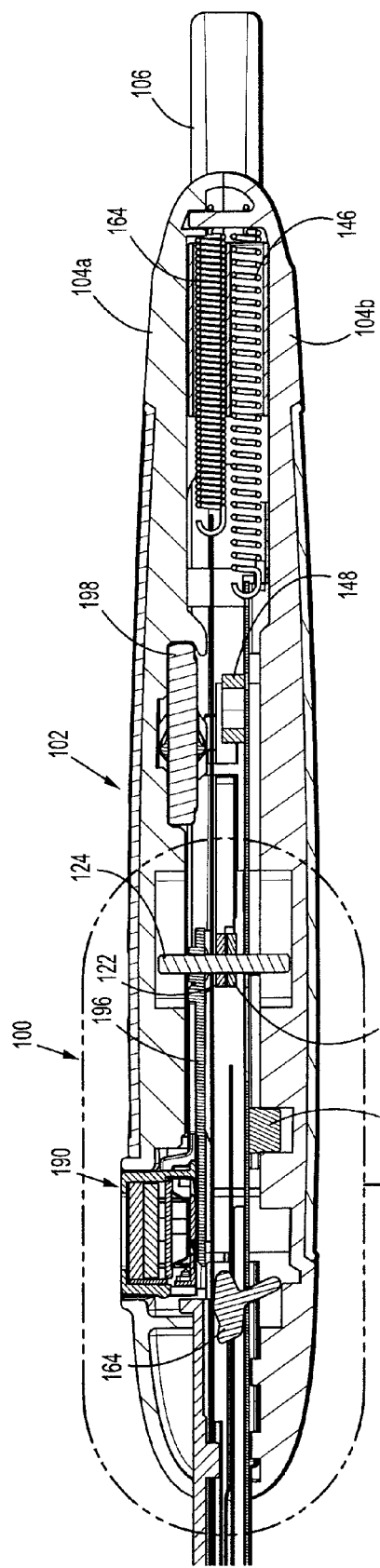
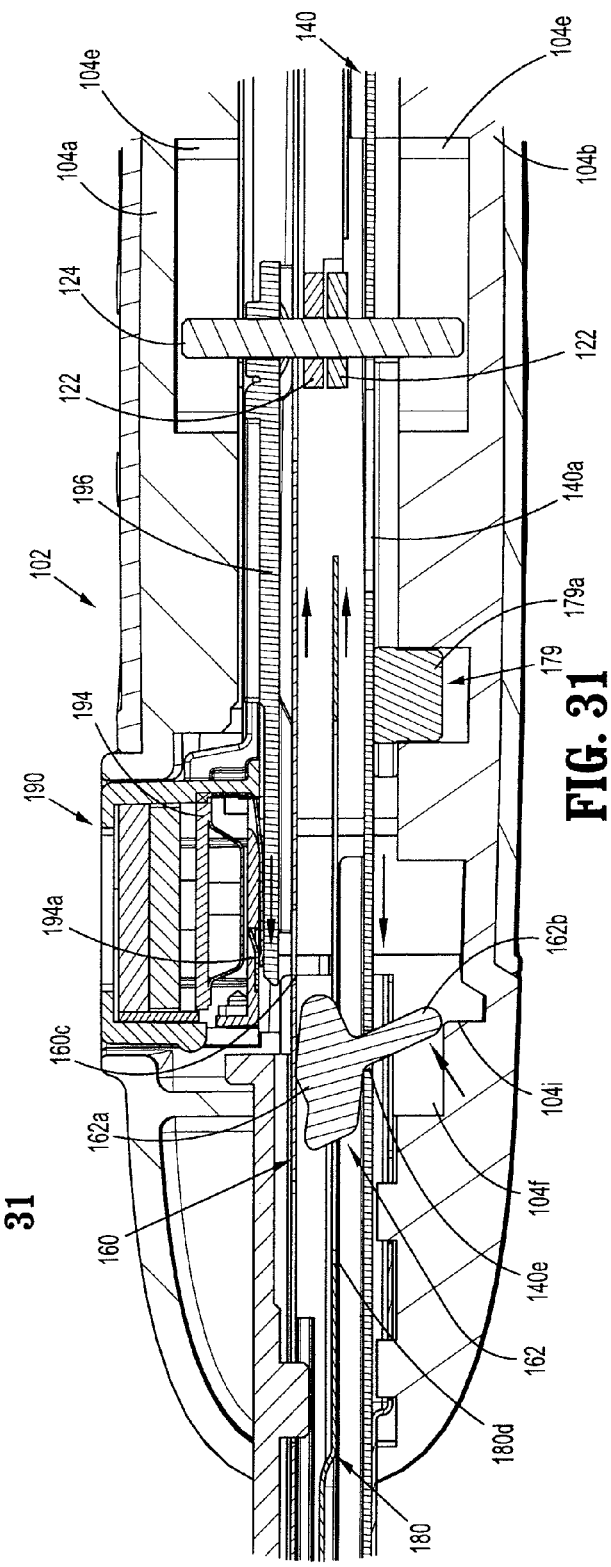

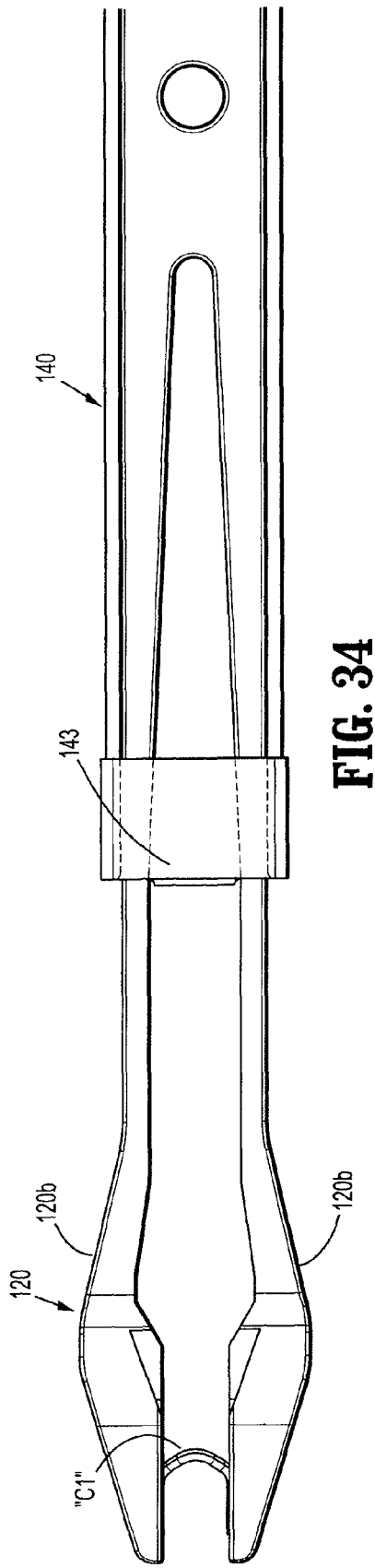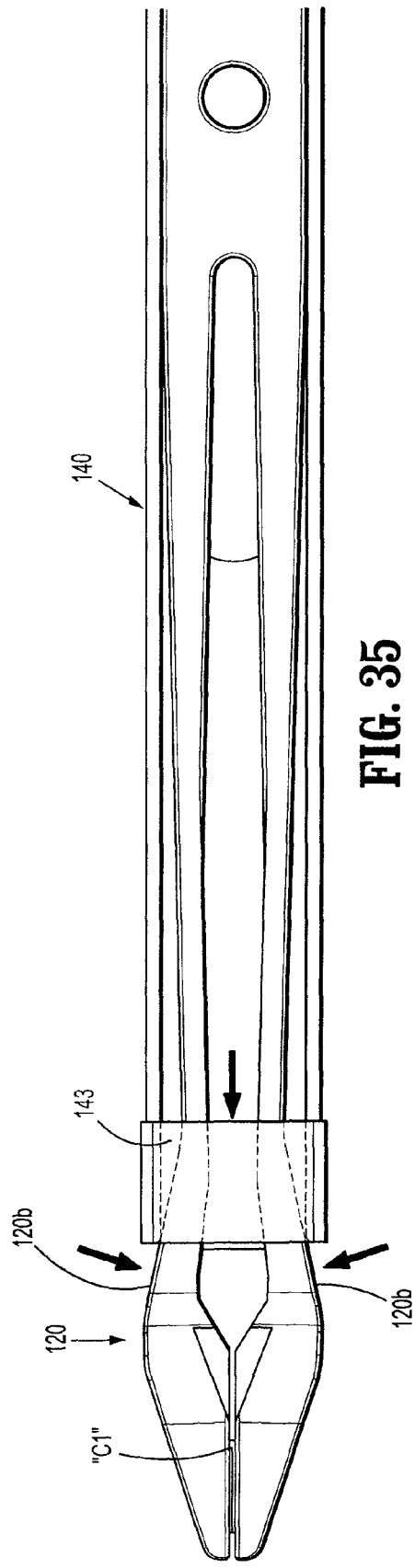

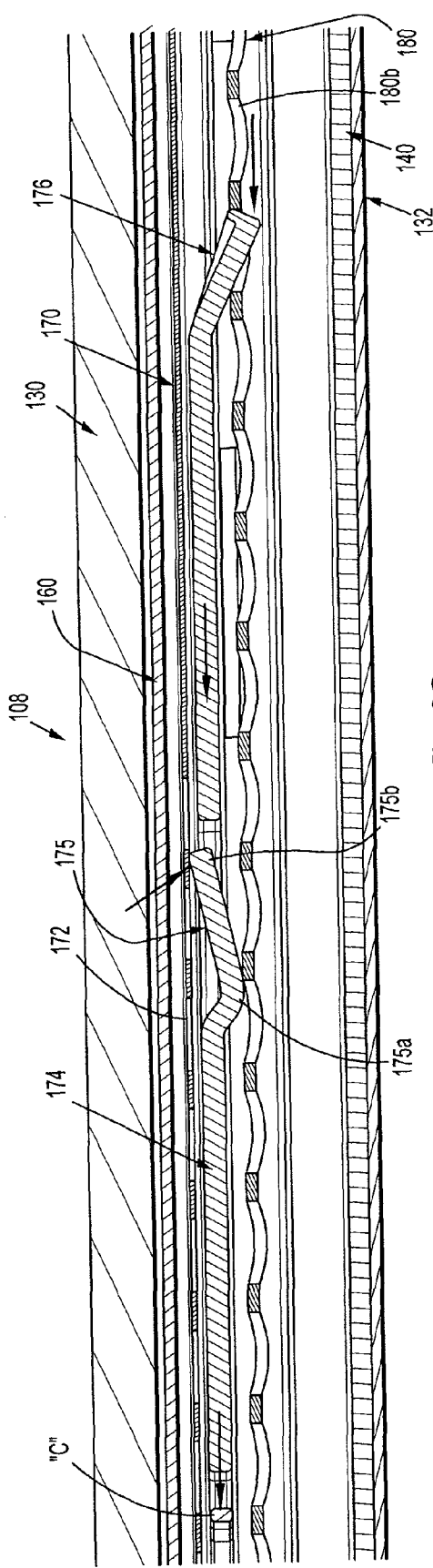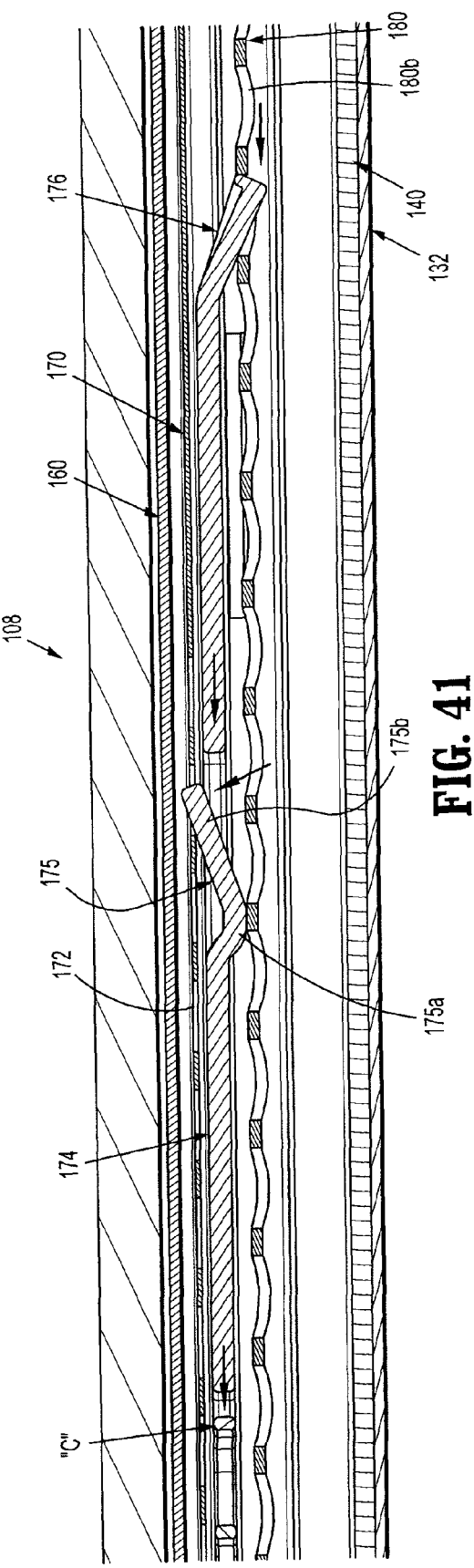

SURGICAL CLIP APPLIER

CROSS-REFERENCE TO RELATED APPLICATION

This application is a National Stage Application of PCT/US2008/059859 filed Apr. 10, 2008 under 35 USC §371 (a), which claims priority of U.S. Provisional Patent Application Ser. No. 60/922,946, filed on Apr. 11, 2007, the entire content of which is incorporated herein by reference.

BACKGROUND

1. Technical Field

The present application relates to surgical clip appliers, and in particular relates to instruments having a plurality of clips for applying the clips to body tissues and vessels during surgical procedures.

2. Discussion of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank, III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

Surgical clip appliers in the prior art are known to include some type of lockout mechanism which prevents closing of the handles, and consequentially closing of the jaws if there are no clips present in the instrument. These lockout mechanisms prevent closure of the jaws about tissue, which can traumatize the tissue and perhaps cause serious damage to the tissue or vessel when a clip is not present in the jaws. However, many of the prior art instruments provide a lockout mechanism which interferes with the closure of the jaws, and upon the application of enough force to the handles, the lockout mechanism many times may be defeated. In order to prevent this, complex mechanisms are often provided, resulting in increased cost of manufacture of the instrument.

In addition, many of the prior art instruments provide complex mechanical arrangements for closing the jaws while simultaneously preparing for feeding the next clip into the jaws after the clip positioned between the jaws is deformed and then released. These complex mechanisms, such as that shown in U.S. Pat. No. 5,431,668 to Burbank, III et al., require numerous parts which increases the cost of manufacture, as well as increasing the time it takes to assemble each instrument. In addition, these instruments generally drive a first component, such as the channel assembly, in one direction to close the jaws while simultaneously drawing the clip pusher bar in an opposite direction to prepare for feeding the next clip in the series of clips to the jaw mechanism. This arrangement typically requires additional moving parts, also tending to increase the cost of manufacture and increase the time of assembly.

The need therefore exists for an instrument for applying surgical clips which reduces the number of parts, and consequently reduces the cost of the instrument, while at the same time reducing the amount of time needed to assemble the instrument during manufacture. A specific need exists for an instrument which minimizes the number of moving parts and synchronizes the moving parts so that they move in the same direction upon closing and opening of the handles. By minimizing the number of moving parts, and synchronizing the direction of movement of the moving parts, the instrument becomes sturdier and easier to manipulate during the surgical procedure.

The need also exists for an instrument having a lockout mechanism which both prevents closing of the jaws by providing a reliable blocking mechanism, while at the same time providing a mechanism for rendering the instrument inoperable upon the application of a predetermined force to the handles after all the clips in the instrument have been utilized during the surgical procedure.

SUMMARY

The present disclosure relates generally to surgical clip appliers. According to an aspect of the present disclosure a surgical clip applier is provided including a housing; a pair of handles pivotably connected to opposite sides of the housing; a channel assembly fixed to and extending from the housing; a clip carrier disposed within said channel assembly and defining a channel and a plurality of windows; a wedge plate slidably disposed within said channel assembly, said wedge plate being operatively connected to said handles and including a plurality of apertures formed along a length thereof; a plurality of clips slidably disposed within said channel of said clip carrier; and a clip follower slidably disposed within said channel of said clip carrier at a location proximal of said plurality of clips. The clip follower is configured and adapted for selective engagement with said windows of said clip carrier and said apertures of said wedge plate. The clip follower is configured and adapted to distally urge said plurality of clips relative to said clip carrier upon a distal advancement of said wedge plate.

The clip applier may include a jaw assembly including a pair of jaws extending from an end of said channel assembly, opposite said housing. The jaw assembly may be adapted to accommodate a clip therein and may be operable to effect closure of a clip in response to movement of said handles.

The clip applier may include a clip pusher bar slidably positioned within at least one of said housing and said channel assembly, said pusher bar having a first end operatively connected to at least one of said handles and a second end defining a pusher terminating proximate said pair of jaws. The pusher bar may be moved towards said jaws as said handles are approximated in a first direction an initial amount to move said distal-most clip between said jaws. The pusher bar may be configured and adapted to move towards said housing as said handles are approximated an additional amount in said first direction to move said pusher behind a distal-most clip in said plurality of clips.

The clip applier may further include a drive channel slidably disposed within at least one of said housing and said channel assembly. The drive channel may have a first end operatively connected to at least one of said handles and a second end configured and dimensioned to selectively engage said pair of jaws to effectuate closure of said pair of jaws. The drive channel may be moved towards said jaw assembly as said handles are moved in said first direction to move said distal end thereof against said jaws to close said jaws. The drive channel may be moved away from said jaws as said handles are moved in a second direction to move said distal end thereof away from said jaws to allow said jaws to open.

The clip applier may further include a pivot arm operatively connected to said wedge plate and selectively engageable by said drive channel. In use, rotation of said pivot arm, during distal movement of said drive channel, results in proximal movement of said wedge plate.

The clip applier may further include a pusher bar cam pivotably supported on the drive channel and movable therewith. The pusher bar cam may extend through a slot formed in said wedge plate and into a window formed in said pusher bar. In use, as said drive channel is moved distally said pusher bar cam moves said pusher bar distally. Additionally, during distal movement of said drive channel, said pusher bar cam may be rotated relative thereto such that said pusher bar cam disengages from said window of said pusher bar allowing said pusher bar to move proximally.

The wedge plate may be biased to a distal position. The pusher bar and/or the drive channel may be biased to a proximal position.

The clip applier may further include a ratchet mechanism. The ratchet mechanism may include a rack, having a plurality of ratchet teeth, associated with said drive channel; and a pawl, having at least one tooth, disposed at a location to selectively engage said rack. The pawl may be biased into engagement with said rack. In use, as said drive channel is longitudinally reciprocated, said plurality of teeth may pass over said pawl. The pawl may prevent inadvertent return of said drive channel before full actuation of said handles.

The clip applier may further include a lockout disposed in a distal end of said channel assembly. In use, the lockout may be actuated by said clip follower when a last clip is expelled from said clip applier. The lockout may be urged by said clip follower to extend across a path of said drive channel, thereby preventing said drive channel from moving distally.

The clip applier may further include a drive pin operatively received in a pivot point formed in said drive channel to transmit axial forces to said drive channel during movement of said handles. The pivot point may be separated from an elongate slot by at least one lip.

The clip applier may further include a shipping wedge selectively attachable to said housing and being configured and adapted to engage each of said handles.

The clip applier may further include a counter mechanism supported in at least one of said housing and said channel assembly. The counter mechanism may be configured and adapted to display a change in said clip applier upon each actuation of said handles.

The drive channel may be configured and dimensioned to at least partially surround said jaws and said wedge plate. The drive channel may include a strap extending across a distal end thereof for maintaining said jaws and said wedge plate within said drive channel.

According to a further aspect of the present disclosure, a surgical clip applier is provided including a housing; a pair of handles pivotably connected to opposite sides of the housing; a channel assembly fixed to and extending from the housing; a clip carrier disposed within said channel assembly and defining a channel; and a drive channel slidably disposed within at least one of said housing and said channel assembly. The drive channel has a first end operatively connected to at least one of said handles and a second end configured and dimensioned to selectively engage a pair of jaws to effectuate closure of said pair of jaws. The clip applier further includes a plurality of clips slidably disposed within said channel of said clip carrier; a clip follower slidably disposed within said channel of said clip carrier at a location proximal of said plurality of clips; and a lockout disposed in a distal end of said channel assembly. In use, the lockout is actuated by said clip follower when a last clip is expelled from said clip applier. The lockout is urged by said clip follower to extend across a path of said of said drive channel, thereby preventing said drive channel from moving distally.

The clip applier may further include a wedge plate slidably disposed within said channel assembly. The wedge plate may be operatively connected to said handles and may include a plurality of apertures formed along a length thereof. The clip carrier may define a plurality of windows. The clip follower may be configured and adapted for selective engagement with said windows of said clip carrier and said apertures of said wedge plate. The clip follower may be configured and adapted to distally urge said plurality of clips relative to said clip carrier upon a distal advancement of said wedge plate.

The clip applier may further include a jaw assembly having a pair of jaws extending from an end of said channel assembly, opposite said housing. The jaw assembly may be adapted to accommodate a clip therein and may be operable to effect closure of a clip in response to movement of said handles.

The clip applier may further include a clip pusher bar slidably positioned within at least one of said housing and said channel assembly. The pusher bar may have a first end operatively connected to at least one of said handles and a second end defining a pusher terminating proximate said pair of jaws. The pusher bar may be moved towards said jaws as said handles are approximated in a first direction an initial amount to move said distal-most clip between said jaws. The pusher bar may be configured and adapted to move towards said housing as said handles are approximated an additional amount in said first direction to move said pusher behind a distal-most clip in said plurality of clips.

The clip applier may further include a pusher bar cam pivotably supported on the drive channel and movable therewith. The pusher bar cam may extend through a slot formed in said wedge plate and into a window formed in said pusher bar. In use, as said drive channel is moved distally said pusher bar cam may move said pusher bar distally.

In operation, during distal movement of said drive channel, said pusher bar cam may be rotated relative thereto such that said pusher bar cam disengages from said window of said pusher bar allowing said pusher bar to move proximally.

The clip applier may further include a pivot arm operatively connected to said wedge plate and selectively engageable by said drive channel. In use, rotation of said pivot arm, during distal movement of said drive channel, may result in proximal movement of said wedge plate.

The clip applier may still further include a ratchet mechanism. The ratchet mechanism may include a rack, having a plurality of ratchet teeth, associated with said drive channel; and a pawl, having at least one tooth, disposed at a location to selectively engage said rack. The pawl may be biased into engagement with said rack. In use, as said drive channel is longitudinally reciprocated, said plurality of teeth may be passed over said pawl. The pawl may prevent inadvertent return of said drive channel before full actuation of said handles.

The clip applier may further include a drive pin operatively received in a pivot point formed in said drive channel to transmit axial forces to said drive channel during movement of said handles. The pivot point may be separated from an elongate slot by at least one lip.

The drive channel may be configured and dimensioned to at least partially surround said jaws and said wedge plate. The drive channel may include a strap extending across a distal end thereof for maintaining said jaws and said wedge plate within said drive channel.

BRIEF DESCRIPTION OF THE DRAWINGS

The present clip applier will be more fully appreciated as the same becomes better understood from the following detailed description when considered in connection with the following drawings, in which:

FIG. 1 is a perspective view of a surgical clip applier according to the present disclosure;

FIG. 2 is a top, plan view of the clip applier of FIG. 1;

FIG. 3 is a side, elevational view of the clip applier of FIGS. 1 and 2;

FIG. 5 is a cross-sectional view of the clip applier of FIGS. 1-4, as taken through 5-5 of FIG. 2;

FIG. 6 is an enlarged view of the indicated area of detail of FIG. 5;

FIG. 7 is an enlarged view of the indicated area of detail of FIG. 5;

FIG. 8 is an enlarged view of the indicated area of detail of FIG. 5;

FIG. 9 is a cross-sectional view of the clip applier of FIGS. 1-8, as taken through 9-9 of FIG. 8;

FIG. 10 is a top, perspective view of the clip applier of FIGS. 1-9 with an upper housing half removed therefrom;

FIG. 15 is a top, perspective view of the distal end of the clip applier of FIGS. 1-14 with the cartridge cover, the pusher bar and a clip carrier removed therefrom;

FIG. 16 is top, perspective view of the distal end of the clip applier of FIGS. 1-15 with the cartridge cover, the pusher bar, the clip carrier, a stack of clips and a clip follower removed therefrom;

FIG. 17 is an enlarged view of the indicated area of detail of FIG. 16;

FIG. 28 is an enlarged view of the indicated area of detail 7 of FIG. 5, during the squeezing of the handles;

FIG. 29 is an enlarged view of the indicated area of detail 8 of FIG. 5, during the squeezing of the handles;

FIG. 30 is a cross-sectional view of the handle assembly of the clip applier of FIGS. 1-29, as taken through 5-5 of FIG. 2, during the squeezing of the handles;

FIG. 31 is an enlarged view of the indicated area of detail of FIG. 30;

FIGS. 34 and 35 are top, plan view of the jaw assembly of the clip applier of FIGS. 1-33, illustrating a closing of the jaw assembly during a squeezing of handles;

FIGS. 40 and 41 are enlarged views of the indicated area of detail 7 of FIG. 5, during the opening of the handles;

DETAILED DESCRIPTION OF EMBODIMENTS

Figure 4:
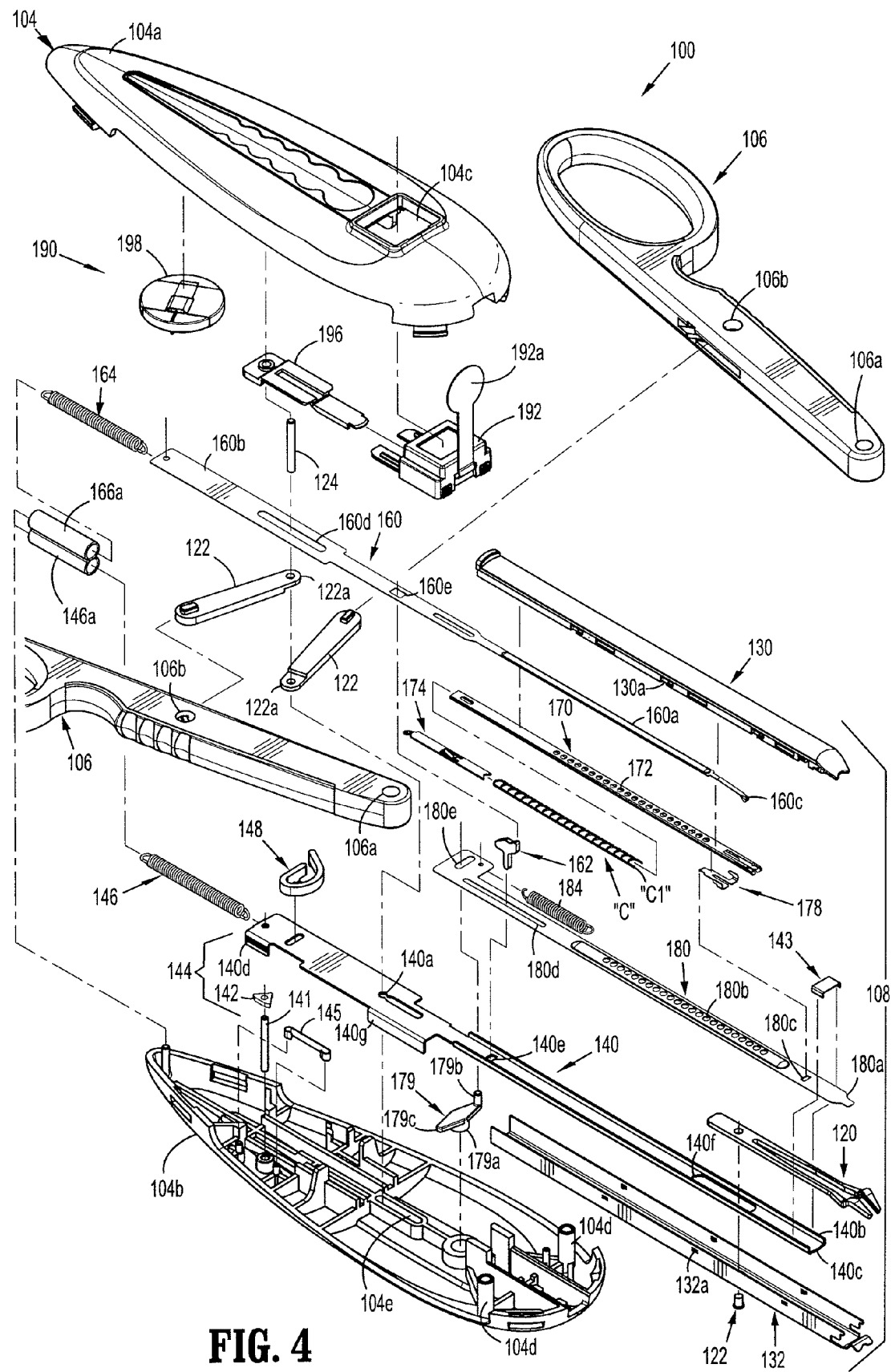
FIG. 4 is a perspective view with parts separated of the clip applier of FIGS. 1-3.
Figure 11:
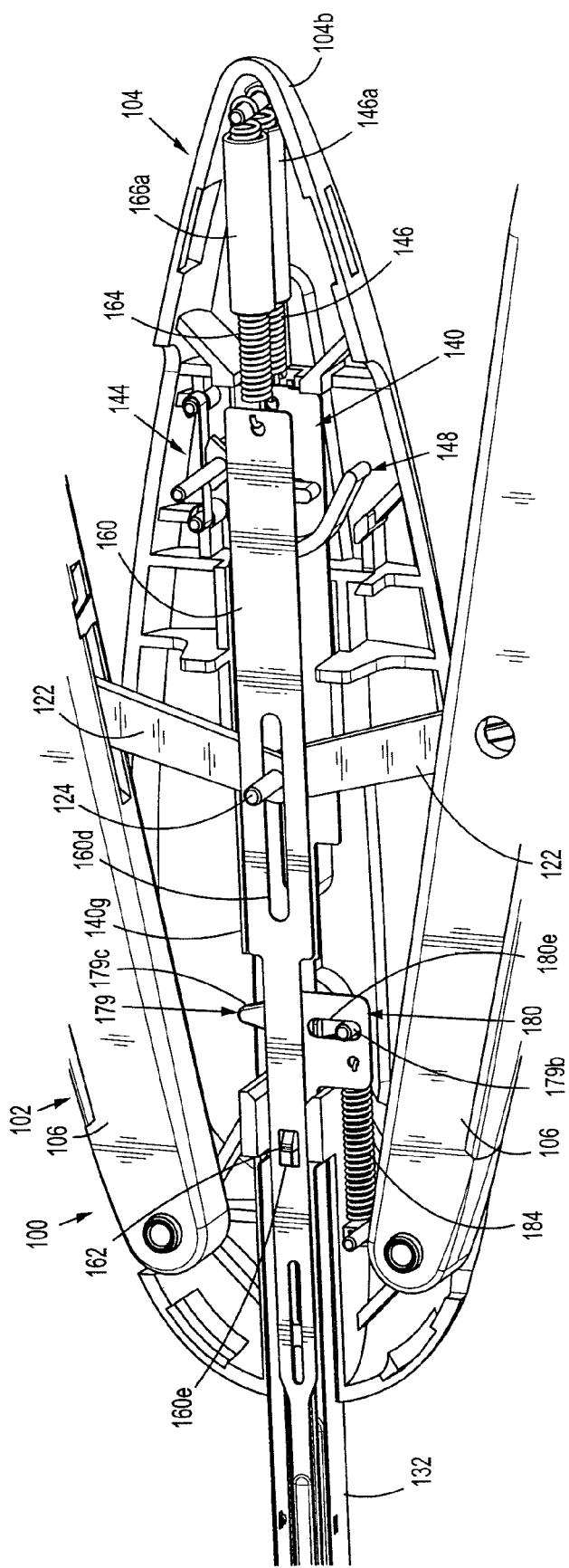
FIG. 11 is a top, perspective view of the clip applier of FIGS. 1-10 with the upper housing half and a counter assembly removed therefrom.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-5, a surgical clip applier in accordance with an embodiment of the present disclosure is generally designated as 100. Surgical clip applier 100 generally includes a handle assembly 102 and a handle assembly 102 including a housing 104 having an upper housing half 104a and lower housing half 104b. Handle assembly 102 further includes a pair of handles 106 pivotably secured to housing 104 and extending outwardly therefrom. A channel assembly 108 is fixedly secured to housing 104 and extends outwardly therefrom, terminating in a jaw assembly 110.

As seen in FIGS. 1-5, housing halves 104a and 104b of clip applier 100 fit together by snap fit engagement with one another. Housing 104 defines a window 104c formed in upper housing half 104a for supporting and displaying a counter mechanism, as will be discussed in greater detail below. Housing 104 may be formed of a suitable plastic material.

As seen in FIG. 4, handles 106 are secured to housing 104 by handle pivot posts 104d extending from lower housing half 104b and into respective apertures 106a formed in handles 106. Handle assembly 102 includes a link member 122 pivotally connected to each handle 106 at a pivot point 106b formed in a respective handle 106. A distal end 122a of each link member 122 is pivotally connected to a pivot point 140a formed in a drive channel 140 via a drive pin 124. Each end of drive pin 124 is slidably received in an elongate channel 104e formed in a respective upper and lower housing half 104a, 104b. In use, as will be described in greater detail below, as handles 106 are squeezed, link members 122 push drive channel 140 distally via drive pin 124.

Channel assembly 108 includes a channel or cartridge cover 130 having a proximal end retained in housing assembly 102, e.g., between upper and lower housing halves 104a, 104b, and an outer channel 132 having a proximal end retained in housing assembly 102, e.g., between upper and lower housing halves 104a, 104b. Cartridge cover 130 is configured and dimensioned for snap-fit engagement with outer channel 132. For example, cover 130 may include at least one retention element 130a configured and adapted to selectively engage a complementary or corresponding retention element 132a provided on outer channel 132.

As seen in FIGS. 4-12, clip applier 100 includes a clip pusher bar 160 slidably disposed beneath cartridge cover 130. Pusher bar 160 includes a distal end 160a defining a pusher 160c configured and adapted to selectively engage/move a distal-most clip "C1" stored in surgical clip applier 100. Pusher bar 160 further includes a proximal end 160b defining a proximal window 160d therein for slidably receiving drive pin 124 therein. Pusher bar 160 further defines a distal window 160e therein for operative engagement with a pusher bar cam 162, as will be discussed in greater detail below.

Clip applier 100 includes a biasing member 164, in the form of a tension spring, operatively secured to and between proximal end 160b of pusher bar 160 and housing 104, tending to maintain pusher bar 160 in a retracted or proximal-most position. Biasing member 164 functions to retract or facilitate retraction of pusher bar 160 following advancement of a distal-most clip "C1" into or between jaws 120. In an embodiment, biasing member 164 is slidably disposed within a sleeve 166a.

Clip applier 100 further includes a pusher bar cam 162 operatively disposed beneath pusher bar 160 and operatively associated with distal window 160e of pusher bar 160. Pusher bar cam 162 includes a head portion 162a operatively received within distal window 160e of pusher bar 160 and a tail or stem portion 162b extending from head portion 162a in a direction toward lower housing half 104b. As seen in FIG. 6, stem portion 162b is slidably received in an elongate slot 104f defined in lower housing half 104b. The function and operation of pusher cam bar 162 will be discussed in greater detail below.

Clip applier 100 further includes a clip carrier 170 disposed within channel assembly 108 and beneath pusher bar 160. Clip carrier 170 is generally a box-like structure having an upper wall 170a, a pair of side walls 170b and a lower wall 170c defining a channel 170d therethrough. Clip carrier 170 includes a plurality of spaced apart windows 172 formed in upper wall 170a and extending longitudinally along a length thereof. Clip carrier 170 includes an elongate window 174 (see FIG. 9) formed in lower wall 170c and extending longitudinally along a length thereof.

As seen in FIGS. 4, 7, 14 and 15, a stack of surgical clips "C" is loaded and/or retained within channel 170d of clip carrier 170 in a manner so as to slide therewithin and/or therealong. Channel 170d is configured and dimensioned to slidably retain a stack or plurality of surgical clips "C" in tip-to-tail fashion therewithin.

Figure 12:
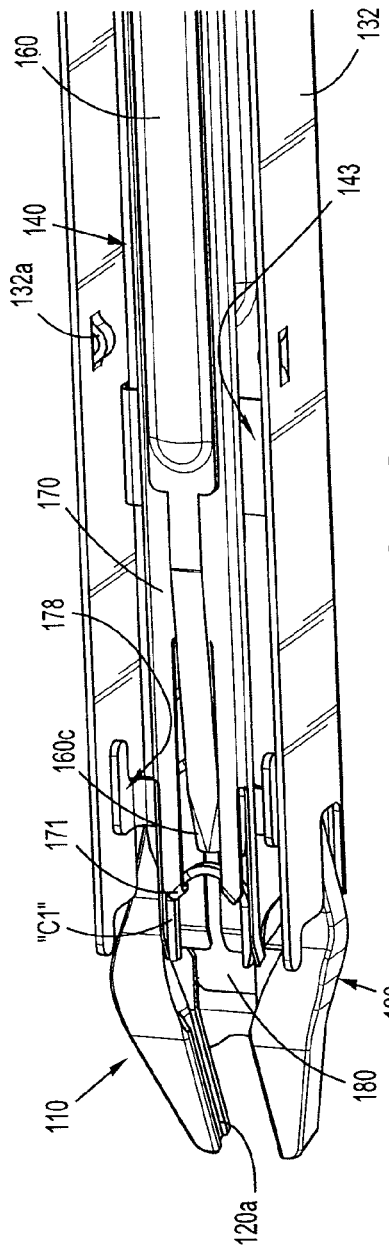
FIG. 12 is a top, perspective view of a distal end of the clip applier of FIGS. 1-11 with a cartridge cover removed therefrom.
Figure 13:
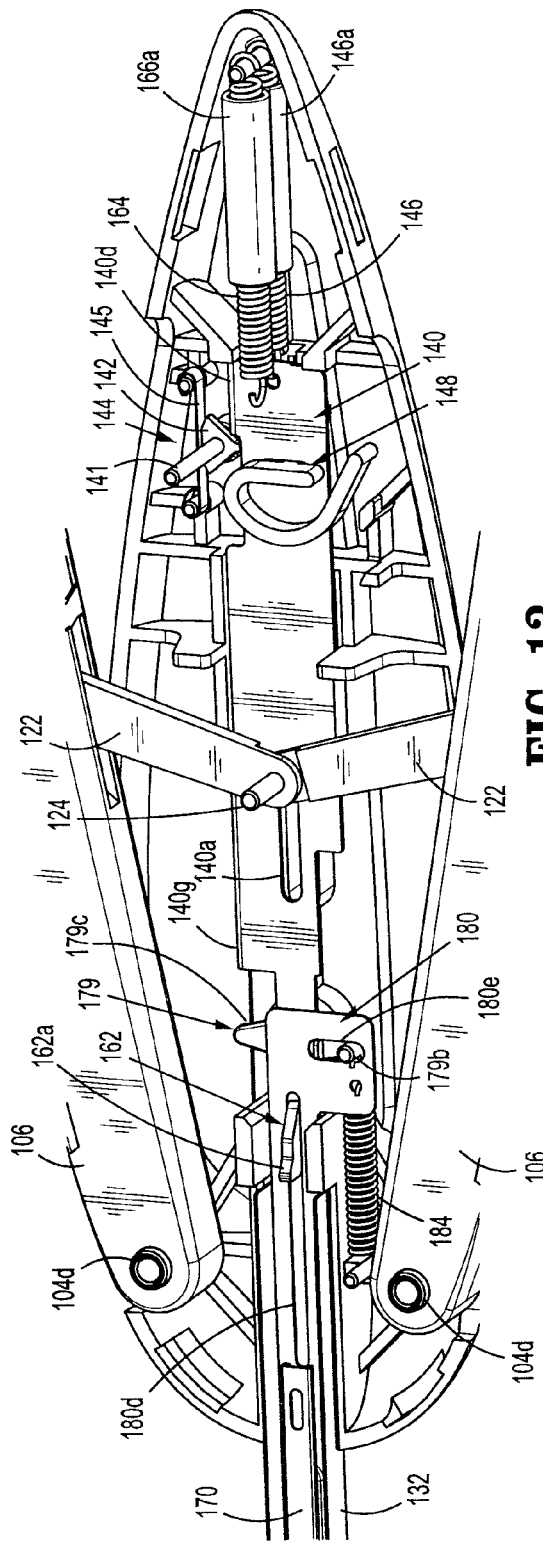
FIG. 13 is a top, perspective view of the clip applier of FIGS. 1-12 with the upper housing half, the counter assembly and a pusher bar removed therefrom.
Figure 14:
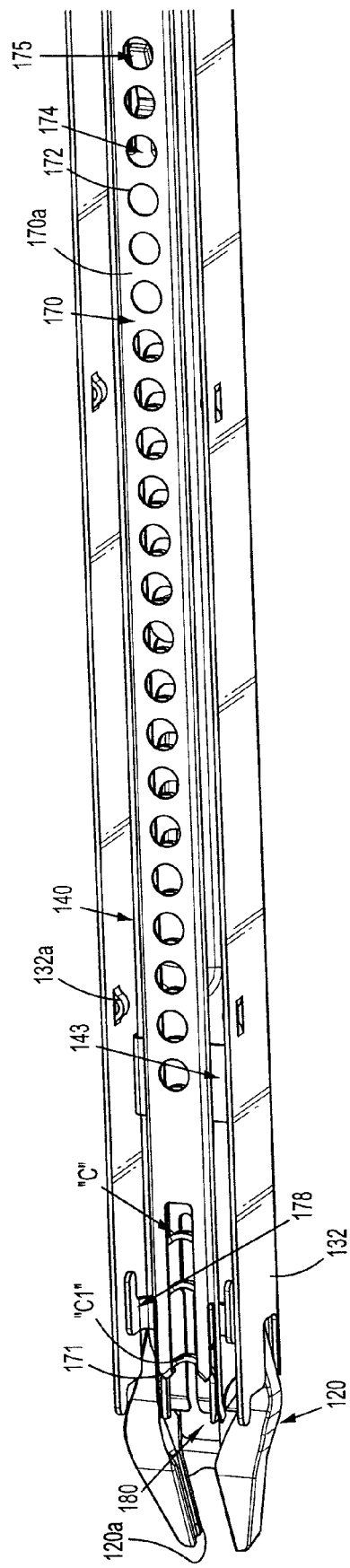
FIG. 14 is a top, perspective view of the distal end of the clip applier of FIGS. 1-13 with the cartridge cover and the pusher bar removed therefrom.
Figure 18:
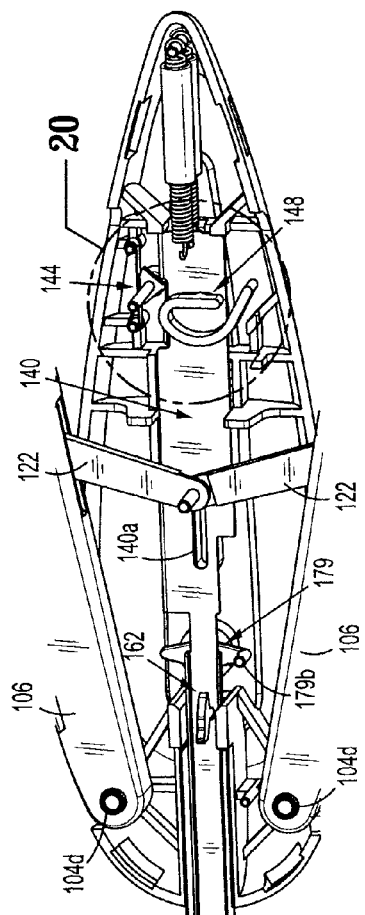
FIG. 18 is a top, perspective view of the clip applier of FIGS. 1-17 with the upper housing half, the counter assembly, the pusher bar, the clip carrier, the stack of clips, the clip follower and a wedge plate removed therefrom.
Figure 19:
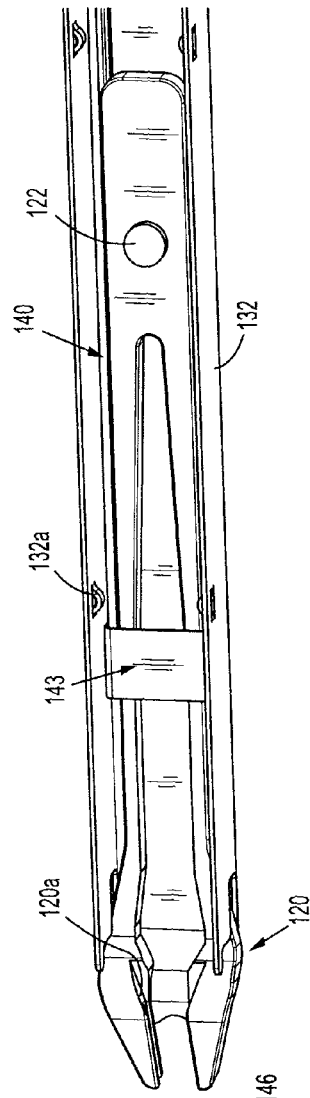
FIG. 19 is an enlarged view of the indicated area of detail of FIG. 18.
Figure 20:
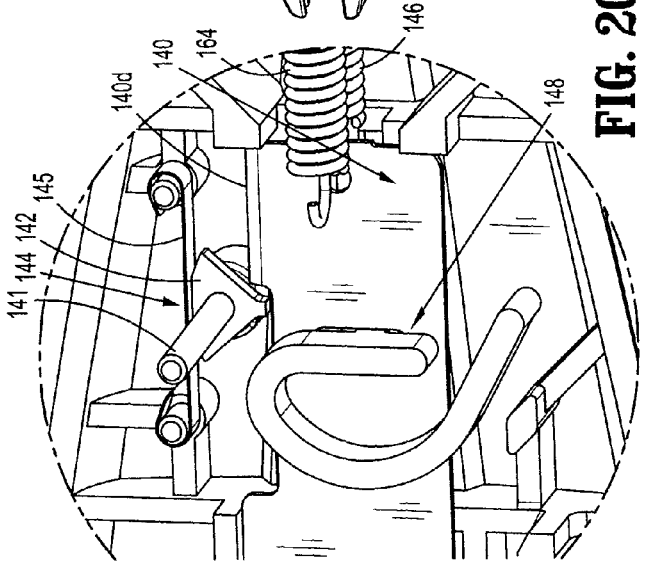
FIG. 20 is an enlarged view of the indicated area of detail of FIG. 18.
Figure 21:
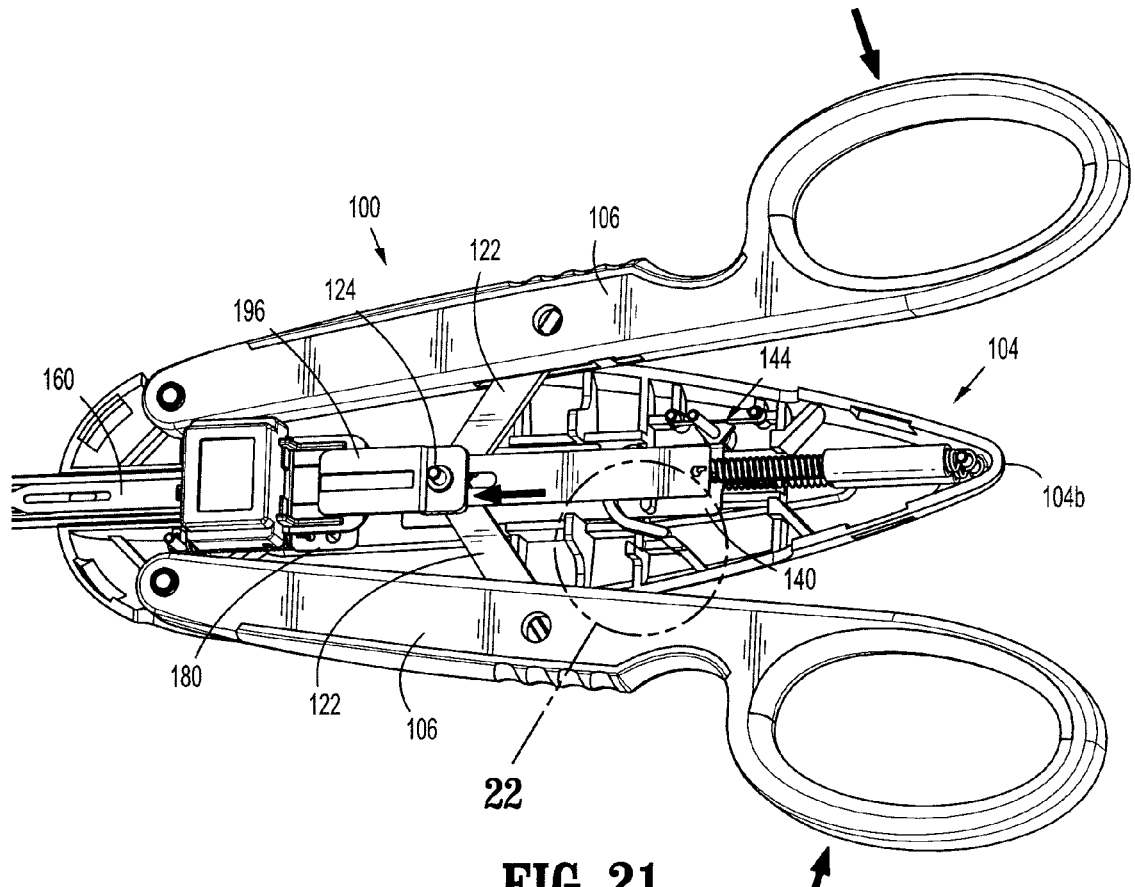
FIG. 21 is a top, perspective view of the clip applier of FIGS. 1-20, with the upper housing half removed therefrom, illustrating the clip applier during an initial squeezing of the handles.

As seen in FIGS. 8, 12 and 14, a distal end of clip carrier 170 includes a pair of spaced apart, resilient tangs 171. Tangs 171 are configured and adapted to selectively engage a backspan of a distal-most surgical clip "C1" of the stack of surgical clips "C" retained within carrier 170.

As seen in FIGS. 4, 7, 14 and 15, clip applier 100 further includes a clip follower 174 slidably disposed within channel 170d of clip carrier 170. As will be discussed in greater detail below, clip follower 174 is positioned behind the stack of surgical clips "C" and is provided to urge the stack of clips "C" forward during an actuation of clip applier 100. As will be described in greater detail below, clip follower 174 is actuated by the reciprocating forward and backward motion of wedge plate 180.

As seen in FIG. 7, clip follower 174 includes body portion 174a defining a plane, a distal tab 175 extending substantially upwardly and rearwardly from body portion 174a, and a proximal tab 176 extending substantially downwardly and rearwardly from body portion 174a. Distal tab 175 includes a distal portion 175a extending downwardly below the plane defined by body portion 174a and a proximal portion 175b extending upwardly above the plane defined by body portion 174a.

Proximal portion 175b of distal tab 175 is configured and dimensioned to selectively engage windows 172 formed in upper wall 170a of clip carrier 170. In use, engagement of proximal portion 175b of distal tab 175 of clip follower 174 in a window 172 formed in upper wall 170a of clip carrier 170 prevents clip follower from traveling or moving in a proximal direction.

Proximal tab 176 is configured and dimensioned to selectively engage windows 180b formed in wedge plate 180. In use, engagement of proximal tab 176 of clip follower 174 in a window 180b formed in wedge plate 180 allows for clip follower 174 to be advanced or moved distally upon a distal movement of wedge plate 180.

As seen in FIGS. 4 and 7-17, clip applier 100 further includes a wedge plate 180 slidably disposed within handle assembly 102 and channel assembly 108. Wedge plate 180 is disposed adjacent to clip carrier 170. Wedge plate 180 includes a substantially tapered distal end 180a for selective operative interposition between jaws 120. As seen in FIGS. 4 and 16, wedge plate 180 defines a plurality of spaced apart windows or apertures 180b and extending longitudinally along a length thereof, a distal window or aperture 180c located distal of apertures 180b, an elongate longitudinally extending slot 180d located proximal of apertures 180c, and a proximal-most transversely oriented slot 180e located proximal of slot 180d.

As seen in FIGS. 4, 8, 12 and 14-16, clip applier 100 includes a distal lockout 178 supported on wedge plate 180. Distal lockout 178 includes a tail or tab 178a extending substantially rearwardly and downwardly and being configured and dimensioned for receipt in distal window or aperture 180c of wedge plate 180.

As seen in FIGS. 4, 6, 10, 11, 13 and 18, clip applier 100 includes a wedge plate pivot arm 179 having a boss 179a pivotally supported in handle assembly 102. In particular, pivot arm 179 is pivotally supported in lower housing half 104b of housing 104. Pivot arm 179 includes a stem or finger 179b extending therefrom and being configured and adapted for slidable engagement in proximal-most slot 180e of wedge plate 180. In use, as will be discussed in greater detail below, as drive channel 140 is moved distally, a flange or wall 140g of drive channel 140 engages against a cam surface 179c of pivot arm 179, opposite stem 179b, causing pivot arm 179 to pivot about boss 179a and cause stem 179b to move wedge plate 180 in a direction opposite to drive channel 140.

Clip applier 100 further includes a biasing member 184, in the form of a tension spring, operatively secured to and between a proximal end of wedge plate 180 and housing 104, tending to maintain wedge plate 180 in an advanced or distal-most position. Biasing member 184 functions to advance or facilitate advancement of wedge plate 180 following formation of a clip "C" positioned between jaws 120. As wedge plate 180 is advanced, as will be discussed hereinbelow, wedge plate 180 cams against an inner surface of jaws 120 to thereby maintain jaws 120 spaced apart from one another.

As seen in FIGS. 4-20, clip applier 100 includes a drive channel 140 reciprocally supported in and extending between housing 104 of handle assembly 102 and channel assembly 108. A proximal end of a drive channel 140 is supported between upper and lower housing halves 104a, 104b of housing 104 and a distal end of drive channel 140 is supported between cartridge cover 130 and outer channel 132 of channel assembly 108, at a location below wedge plate 180.

A distal end of drive channel 140 is a substantially U-shaped channel including a pair of spaced apart side walls 140b extending from a backspan 140c thereof, in a direction away from outer channel 132 and toward cartridge cover 130. Drive channel 140 further defines a drive pin recess 140a formed in backspan 140c for pivotally and/or slidably receiving drive pin 124 therethrough. Drive channel 140 further defines a pusher bar cam aperture 140e formed in backspan 140c at a location distal of drive pin recess 140a. Drive channel 140 further defines a reciprocation limiting slot 140f formed in backspan 140c at a location distal of pusher bar cam aperture 140e.

Clip applier 100 includes a drive channel strap 143 secured to drive channel 140. Strap 143 is secured to uprights 140b of drive channel 140 so as to extend transversely thereacross. In one embodiment, strap 142 is secured to drive channel 140 at a location distal of reciprocation limiting slot 140f. As seen in FIGS. 8 and 14-16, strap 143 is secured to drive channel 140 such that wedge plate 180 extends beneath strap 143.

Clip applier 100 further includes an audible/tactile indicator 148 supported on drive channel 140. In use, as will be described in greater detail below, as clip applier 100 is actuated and drive channel 140 is reciprocated, indicator 148 interacts with corresponding complementary structure provided in clip applier 100 to create an audible and/or a tactile feedback to the user.

Clip applier 100 further includes a biasing member 146, in the form of a tension spring, operatively secured to and between a proximal end of drive channel 140 and housing 104, tending to maintain drive channel 140 in a retracted or proximal-most position. Biasing member 146 functions to retract or facilitate retraction of drive channel 140 following formation of a clip "C" positioned between jaws 120. In an embodiment, biasing member 146 is slidably disposed within a sleeve 146a.

A proximal end of drive channel 140 includes or defines a ratchet rack 140d configured and adapted to engagement with a ratchet pawl 142. Rack 140d of drive channel 140 and pawl 142 define a ratchet mechanism 144. In use, as drive channel 140 is moved axially, rack 140d is also moved. Rack 140d has a length which allows pawl 142 to reverse and advance back over rack 140d when rack 140d changes between proximal and distal movement as drive channel reaches a proximal-most or distal-most position.

Pawl 142 is pivotally connected to lower housing half 104b by a pawl pin 141 at a location wherein pawl 142 is in substantial operative engagement with rack 140d. Pawl 142 is engageable with rack 140d to restrict longitudinal movement of rack 140d and, in turn, drive channel 140. Ratchet mechanism 144 further includes a pawl spring 145 configured and positioned to bias pawl 142 into operative engagement with rack 140d. Pawl spring 145 functions to maintain the teeth of pawl 142 in engagement with the teeth of rack 140d, as well as to maintain pawl 142 in a rotated or canted position.

Surgical clip applier 100 includes a pair of jaws 120 mounted on or at a distal end of channel assembly 108 and actuatable by a handles 106 of handle assembly 102. Jaws 120 are formed of a suitable biocompatible material such as, for example, stainless steel or titanium.

Jaws 120 are mounted in a distal end of drive channel 140 via a rivet 122 or the like extending through reciprocation limiting slot 140f of drive channel 140 such that jaws 120 are longitudinally stationary relative to outer channel 132 and drive channel 140.

As seen in FIGS. 8, 12 and 14-17, jaws 120 define a channel 120a therebetween for receipt of a surgical clip (not shown) therein.

As seen in FIGS. 1, 2, 4-6 and 10, clip applier 100 further includes a counter mechanism 190 supported in housing 104 of handle assembly 102. Counter mechanism 190 includes a display 192, a processor 194, an actuator 196 and an energy source 198 in the form of a battery or the like.

Display 192 may be any device known in the art to provide an indication of an event. The event may be related to the procedure or the operation of the clip applier 100. Display 192 may be a liquid crystal display (LCD), a plasma display, one or more light emitting diodes (LEDs), a luminescent display, a multi-color display, a digital display, an analog display, a passive display, an active display, a so called "twisted nematic" display, a so called "super twisted nematic" display, a "dual scan" display, a reflective display, a backlit display, an alpha numeric display, a monochrome display, a so called "Low Temperature Polysilicon Thin Film Transistor" (LPTS TFT) display, or any other suitable display 192 that indicates a parameter, information or graphics related to the procedure or clip applier 100.

In one embodiment, display 192 is a liquid crystal display which may be a black & white or color display that displays one or more operating parameters of clip applier 100 to the surgeon. In one embodiment, the operating parameter displayed may be an amount or number of remaining clips, a number of clips that have been used, a position parameter, a surgical time of usage, or any other parameter of the procedure. The display 192 may display text, graphics or a combination thereof.

In one embodiment, counter mechanism 190 may have a tab 192a, preferably made from a Mylar or another polymeric insulating material, disposed between battery or energy source 198 and a contact 194a of processor 194 or between the contacts 194a of processor 194 to prevent the battery or energy source 198 from becoming drained during storage. The tab 192a may extend out of housing 104 of surgical clip applier 100 in order to allow for easy removal of the tab therefrom. Once the tab 192a is removed, battery or energy source 198 comes into electrical contact with the contact 194a of processor 194 or between the contacts 194a of the processor 194.

Display 192 may include a lens or the like for magnifying the parameters displayed thereon. The lens of display 192 may magnify the display to any desired size in order to allow a surgeon to read the display with ease from a distance.

Actuator 196 of counter mechanism 190 is operatively connected to drive pin 124 such that reciprocal axial movement of drive pin 124 results in concomitant axial movement of actuator 196. As actuator 196 is moved in a distal direction, actuator 196 engages contact 194a causing contact 194a to complete a circuit and trigger processor 194 to perform a function (i.e., reduce the number appearing on display 192 by a give increment or value).

With reference to FIGS. 21-46, the operation of surgical clip applier 100, to crimp or form a surgical clip around a target tissue, such as, for example, a vessel, will now be described. Prior to an initial squeezing of handles 106 of clip applier 100, drive pin 124 is located at a proximal-most position, pawl 142 is located proximal of rack 140d of drive channel 140, pusher bar cam 162 is located at a proximal-most position, and no clips "C" are positioned within jaws 106. Since drive pin 124 is at a proximal-most position, pusher bar 160, drive channel 140, and counter actuator 196 are also at a proximal-most position. Also, prior to an initial squeezing of handles 106 of clip applier 100, wedge plate 180 is located at a distal-most position.

Also prior to the initial squeeze, no clips "C" present within jaws 120. A clip "C" is first loaded into jaws 120 during the initial squeezing of handles 106, as will be described in greater detail below.

Referring now to FIGS. 21-25, clip applier 100 is illustrated, with upper housing half 104a removed therefrom, during an initial squeezing of handles 106. As seen in FIGS. 21-25, during an initial squeezing of handles 106, distal ends 122a of link members 122 are caused to be moved distally relative to housing 104. As distal ends 122a of link members 122 are moved distally, drive pin 124 is caused to be moved distally thereby transmitting distal axial movement to drive channel 140 and counter actuator 196. As drive channel 140 is moved distally, pusher bar cam 162 is moved distally thereby concomitantly moving pusher bar 160 distally relative to housing 104 due to the engagement of pusher bar cam 162 in distal window 160e of pusher bar 160. As drive channel 140 and pusher bar 160 are moved distally, respective biasing members 146, 164 are stretched or extended.

Figure 22:
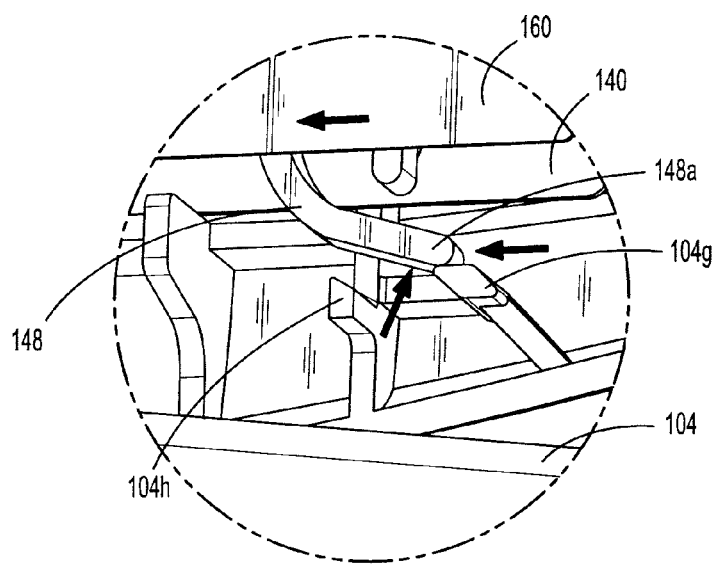
FIG. 22 is an enlarged view of the indicated area of detail of FIG. 21.

As seen in FIG. 22, during the initial squeeze of handles 106, audible/tactile indicator 148 functions to create an audible click and/or a tactile vibration, thereby indicating to the user that handles 106 of surgical clip applier 100 have gone through at least a portion of a stroke. In particular, as handles 106 are actuated, an arm 148a of audible/tactile indicator 148 rides over and/or along a ledge 104g formed in at least one of upper and lower housing halves 104a, 104b and is flexed thereby. As arm 148a of audible/tactile indicator 148 reaches the end of ledge 104g, arm 148a snaps over the end of ledge 104g and comes into contact with a surface 104h of upper and/or lower housing halves 104a, 104b, thereby creating and audible sound and a tactile vibration as arm 148a comes into contact with surface 104h. In an embodiment, audible/tactile indicator 148 indicates to the user that a clip "C" has been appropriately fired.

Figure 23:
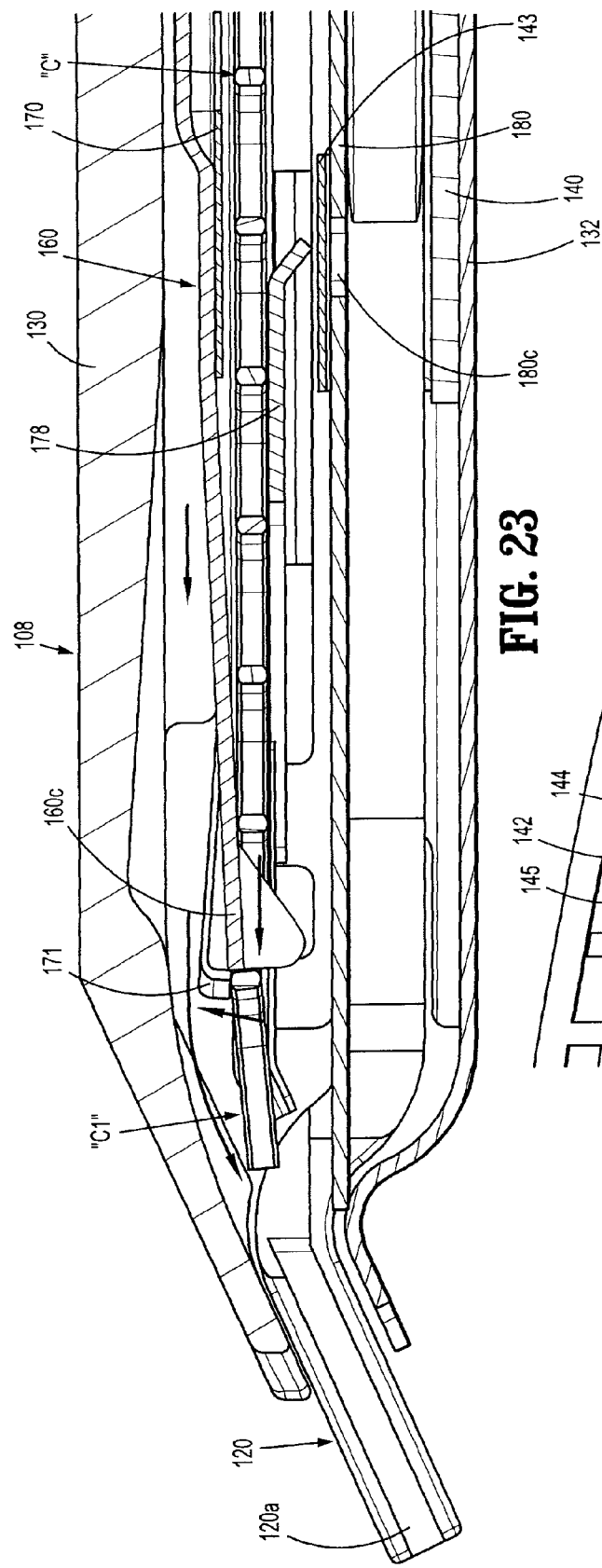
FIG. 23 is an enlarged view of the indicated area of detail 8 of FIG. 5, during the initial squeezing of the handles.

As seen in FIG. 23, also during the initial squeeze of handles 106, as pusher bar 160 is moved in a distal direction, pusher 160c thereof engages a backspan of a distal-most clip "C1" and begins to move or urge distal-most clip "C1" distally out of clip carrier 170 and into jaws 120. As distal-most clip "C1" is moved distally, tangs 171 of clip carrier 170 are deflected or cammed out of engagement with distal-most clip "C1" and return to their un-deflected or un-cammed state to capture a subsequent clip of the stack of clips "C". During the initial squeeze of handles 106, pusher bar 160 is advanced an amount sufficient to place distal-most clip "C1" in channels 120a of jaws 120.

Figure 24:
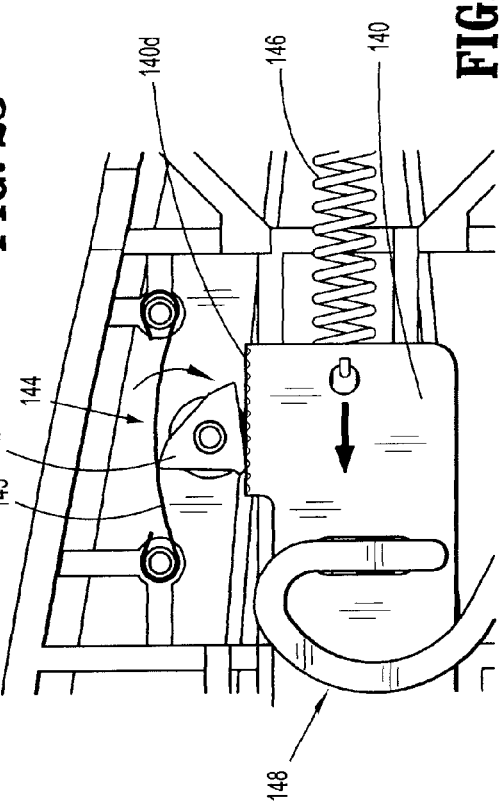
FIG. 24 is an enlarged, plan view of a rack and pawl assembly of the clip applier of FIGS. 1-23, during the initial squeezing of the handles.
Figure 26:
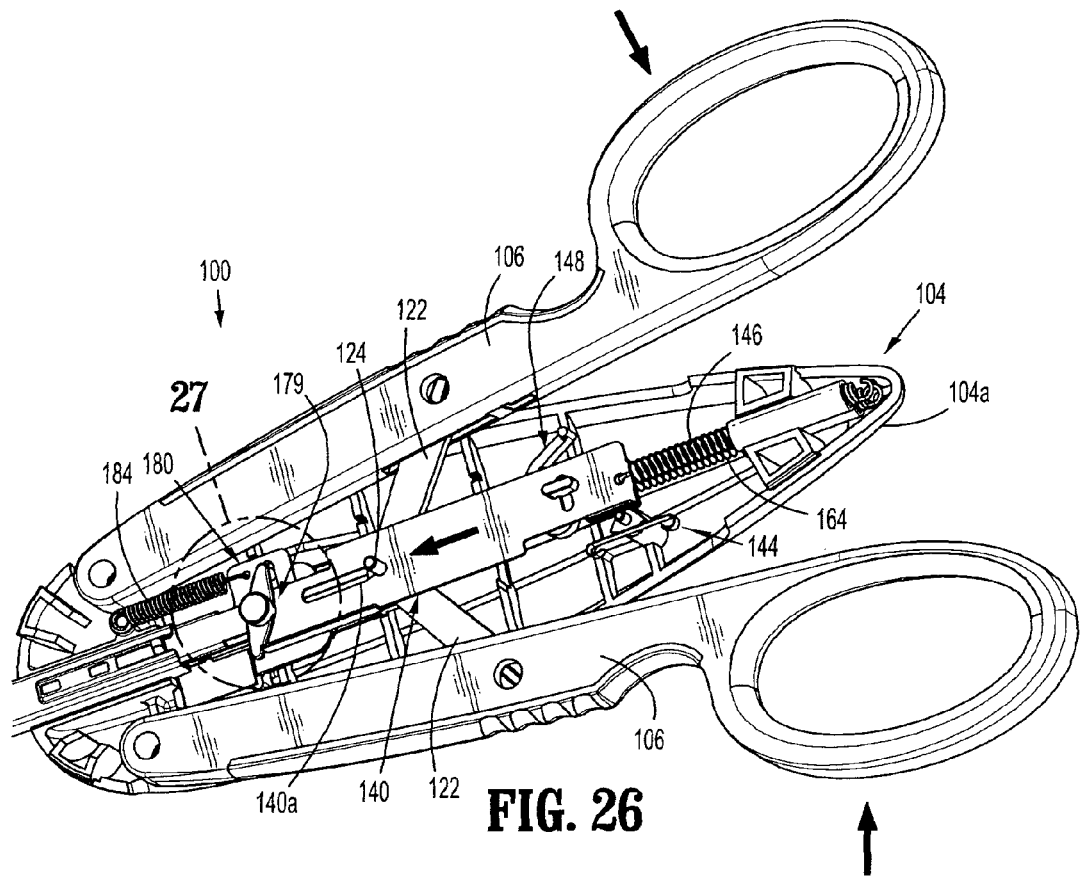
FIG. 26 is a top, perspective view of the clip applier of FIGS. 1-25, with the upper housing half removed therefrom, illustrating the clip applier during a squeezing of the handles.
Figure 27:
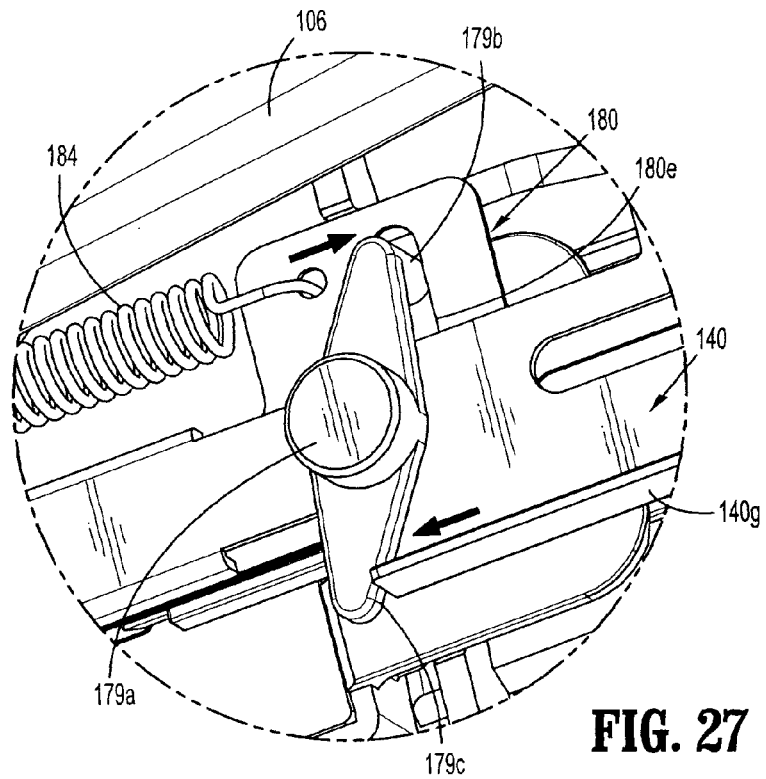
FIG. 27 is an enlarged view of the indicated area of detail of FIG. 26.

As seen in FIG. 24, also during the initial squeeze of handles 106, as drive channel 140 is moved in a distal direction, rack 140d of ratchet mechanism 144 is moved distally causing teeth thereof to move into engagement with and over or across a tooth of pawl 142. Once rack 140d of ratchet mechanism 144 is moved into engagement with pawl 142, drive channel 140 can not return to a home or proximal-most position until rack 140d has cleared pawl 142. During the initial squeeze of handles 106, as seen in FIGS. 26 and 27, drive channel 140 is moved distally until flange or wall 140g of drive channel 140 abuts or engages against cam surface 179c of pivot arm 179.

Figure 25:
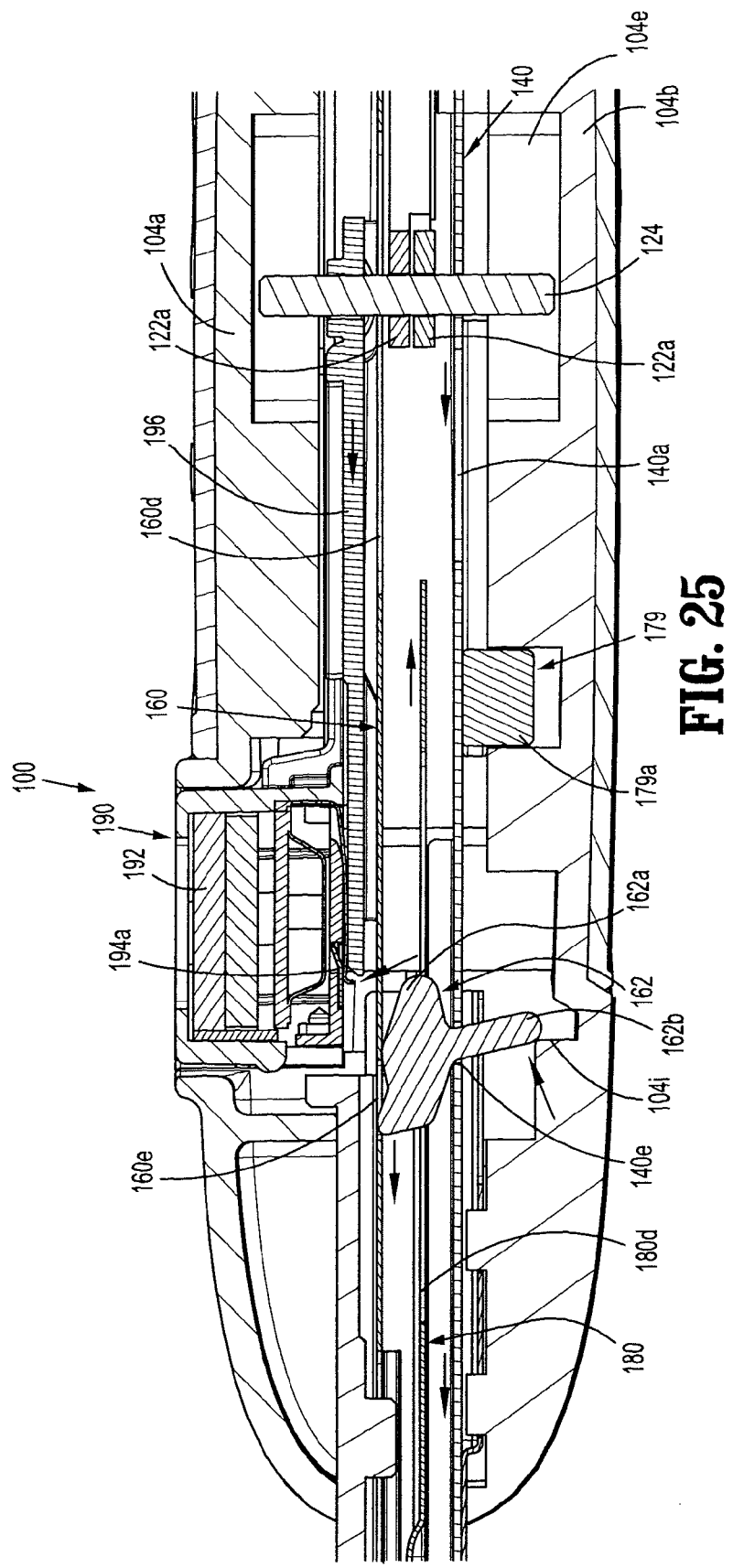
FIG. 25 is an enlarged view of the indicated area of detail 6 of FIG. 5, during the initial squeezing of the handles.

As seen in FIG. 25, during the initial squeeze of handles 106, pusher bar cam 162 is moved distally with drive channel 140, causing pusher bar 160 to move therewith, as described above, until stem portion 162b of pusher bar cam 162 engages or abuts against a ledge 104i formed in elongate slot 104f of lower housing half 104b. When stem portion 162b of pusher bar cam 162 engages against ledge 104i, pusher bar cam 162 is rotated, at window 140e of drive channel 140, thereby causing head portion 162a to begin disengaging or begin rotating out of distal window 160e of pusher bar 160.

With continued reference to FIG. 25, during the initial squeeze of handles 106, with tab 192a removed, counter actuator 196 is moved into engagement with contact 194a of processor 194 thereby completing a circuit and causing processor 194 to perform a function, as described above.

Referring now to FIGS. 26-37, clip applier 100 is illustrated, with lower housing half 104b removed therefrom, during a further squeezing of handles 106. As seen in FIGS. 26-37, during the further squeezing of handles 106, distal ends 122a of link members 122 are caused to be moved further distally relative to housing 104. As distal ends 122a of link members 122 are moved further distally, drive pin 124 is caused to be moved further distally thereby transmitting distal axial movement to drive channel 140 and counter actuator 196.

As seen in FIGS. 26 and 27, as drive channel 140 is moved further distally, flange or wall 140g of drive channel 140 cams against cam surface 179c of pivot arm 179 causing pivot arm 179 to rotate about boss 179a. As pivot arm 179 is rotated about pivot boss 179a, stem 179b of pivot arm 179 is moved in a direction opposite to the direction of motion of cam surface 179c. As stem 179b of pivot arm 179 is moved, stem 179b slidably cams within proximal-most slot 180e of wedge plate 180 causing wedge plate 180 to move in a proximal direction. As seen in FIG. 27, as wedge plate 180 is moved in a proximal direction biasing member 184 is stretched or extended.

As seen in FIGS. 28, 29 and 31, as wedge plate 180 is moved in a proximal direction, a wedge plate 180 is moved proximally relative to clip follower 174 thereby moving windows 180b thereof proximally relative to proximal tab 176 of clip follower 174. Also, as wedge plate 180 is moved in a proximal direction, distal end 180a thereof is withdrawn from between jaws 120, thereby allowing for jaws 120 to eventually be closed or approximated.

Figure 32:
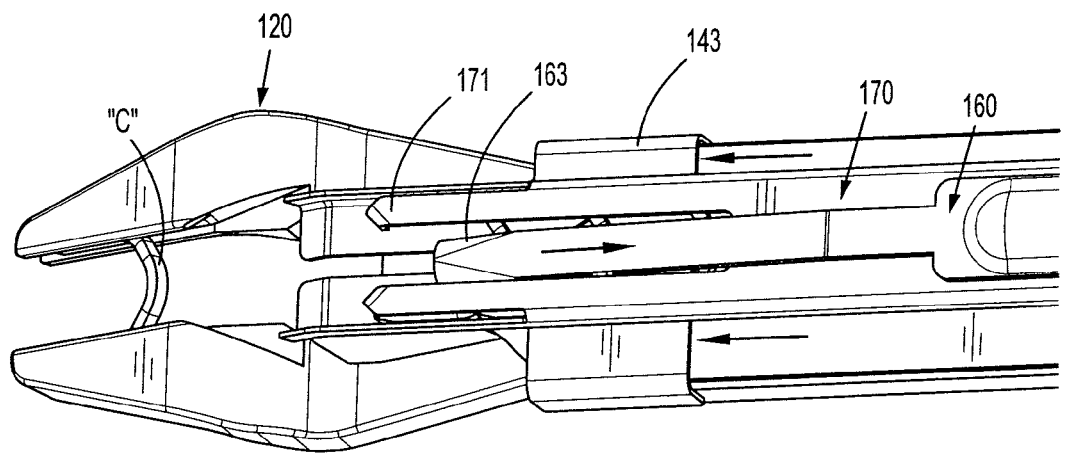
FIG. 32 is a top, perspective view of the distal end of the clip applier of FIGS. 1-31, with the cartridge cover removed therefrom, during the squeezing of the handles.

As seen in FIGS. 31 and 32, as drive channel 140 is moved further distally, pusher bar cam 162 is moved further distally in the manner described above, until stem 162b thereof moves over ledge 104i formed in elongate slot 104f of lower housing half 104b and rotates head portion 162a of pusher bar cam 162 out of engagement of distal window 160e of pusher bar 160. Once head portion 162a of pusher bar cam 162 is disengaged from or rotated out of distal window 160e of pusher bar 160, pusher bar 160 is withdrawn to a proximal-most position due to the spring force exerted thereon by extended biasing member 164.

Figure 33:
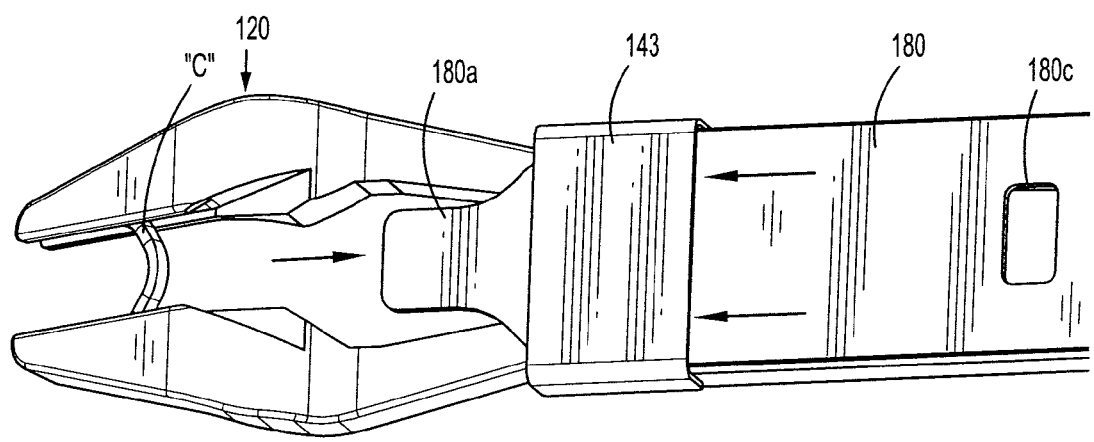
FIG. 33 is a top, perspective view of the distal end of the clip applier of FIGS. 1-32, with the cartridge cover, the pusher bar and the clip carrier removed therefrom, during the squeezing of the handles.
Figure 37:
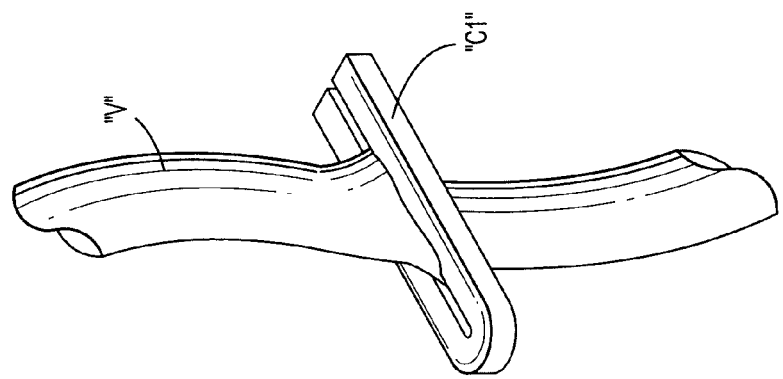
FIG. 37 is a perspective view of a body vessel including a clip of the surgical clip applier, applied thereto.

As seen in FIGS. 32 and 33, as drive channel 140 is moved further distally, with pusher 160c of pusher bar 160 and distal end 180a of wedge plate 180 removed from between jaws 120, a distal edge of drive channel 140 and/or drive channel strap 143 engages against camming surfaces 120b of jaws 120 thus causing jaws 120 to approximate toward one another and to form surgical clip "C1" interposed therebetween. Since drive channel strap 143 is fixed to drive channel 140 and moves therewith, drive channel strap 143 functions to cap drive channel 140 so as to maintain jaws 120 within drive channel 140 during the approximation of jaws 120 and to maintain wedge plate 180 within drive channel 140 during operation of clip applier 100. As seen in FIG. 37, surgical clip "C1" may be formed or crimped onto a vessel "V" or any other biological tissue.

Figure 36:
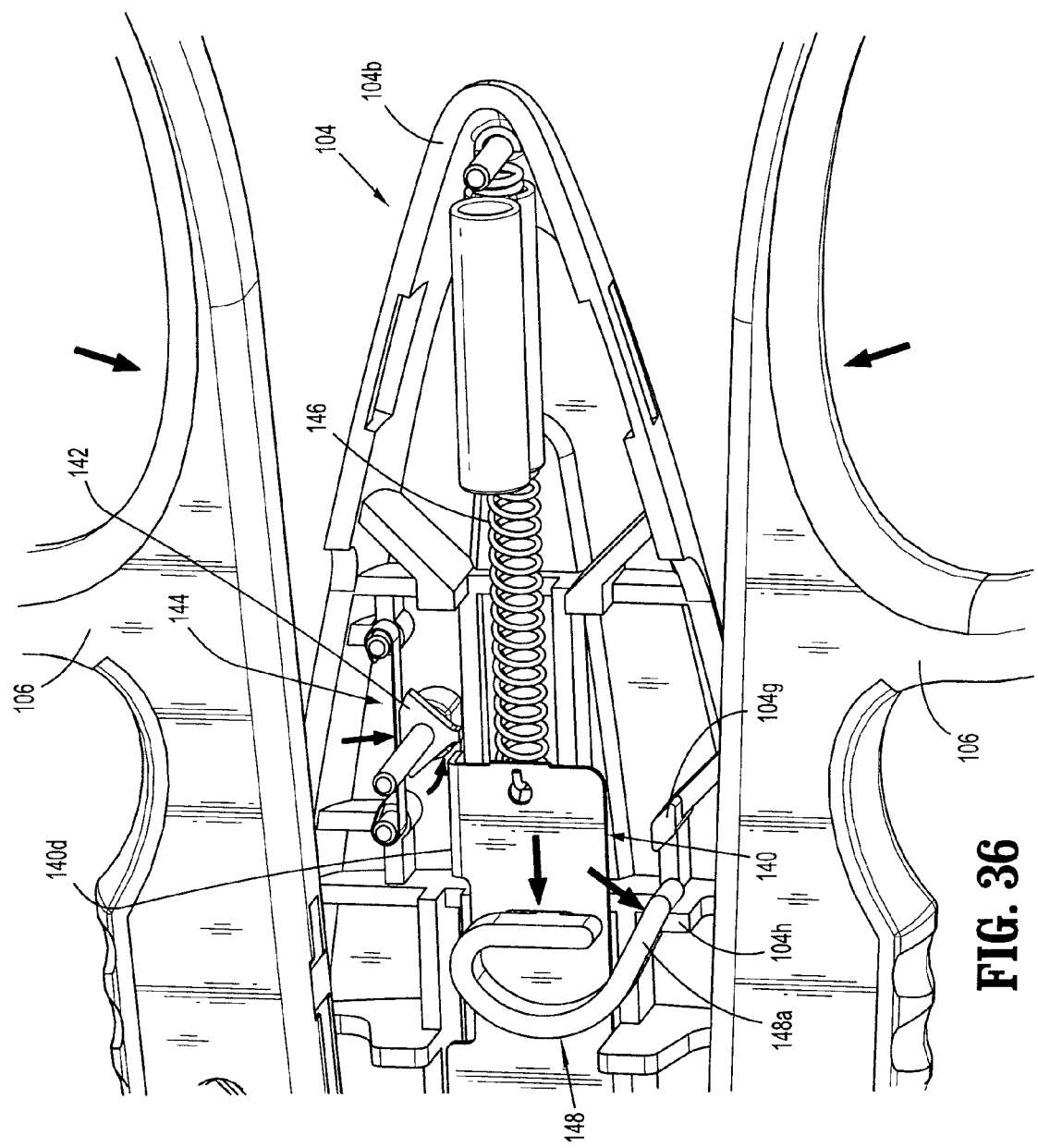
FIG. 36 is a top, perspective view of the clip applier of FIGS. 1-35, with the upper housing half removed therefrom, illustrating an actuation of an audible/tactile feedback member and the rack and pawl assembly.

Also, as drive channel 140 is fully advanced distally, as seen in FIG. 36, rack 140d of ratchet mechanism 144 is moved distally beyond pawl 142 such that the teeth of rack 140d are moved distally of the tooth of pawl 142 thereby disengaging rack 140d and pawl 142 from one another. In this manner, drive channel 140 is permitted to return to a home or proximal-most position.

As described above and as seen in FIG. 36, as drive channel 140 is moved distally, arm 148a of audible/tactile indicator 148 snaps over the end of ledge 104g and comes into contact with a surface 104h of upper and/or lower housing halves 104a, 104b, thereby creating and audible sound and a tactile vibration as arm 148a comes into contact with surface 104h. The audible/tactile feedback may indicate to the surgeon that a clip has been appropriately formed and that clip applier 100 has undergone an acceptable stroke.

Referring now to FIGS. 38-43, clip applier 100 is illustrated following a complete stroke or squeezing of handles 106 and during an opening of handles 106. During an opening or release of handles 106, distal ends 122a of link members 122 are caused to be moved proximally relative to housing 104. As distal ends 122a of link members 122 are moved proximally, drive pin 124 is caused to be moved proximally thereby transmitting proximal axial movement to drive channel 140 and counter actuator 196. The proximal movement of drive channel 140 is facilitated by the constriction of biasing members 146. Alternatively, the release of handles 106 results in biasing member 146 withdrawing drive channel 140 in a proximal direction.

As drive channel 140 is moved proximally, the distal edge of drive channel 140 and/or drive channel strap 143 disengages from against camming surfaces 120b of jaws 120 thus freeing jaws 120 for separation from one another as wedge plate 180 is re-inserted therebetween, and to receive another surgical clip "C" therebetween.

Figure 39:
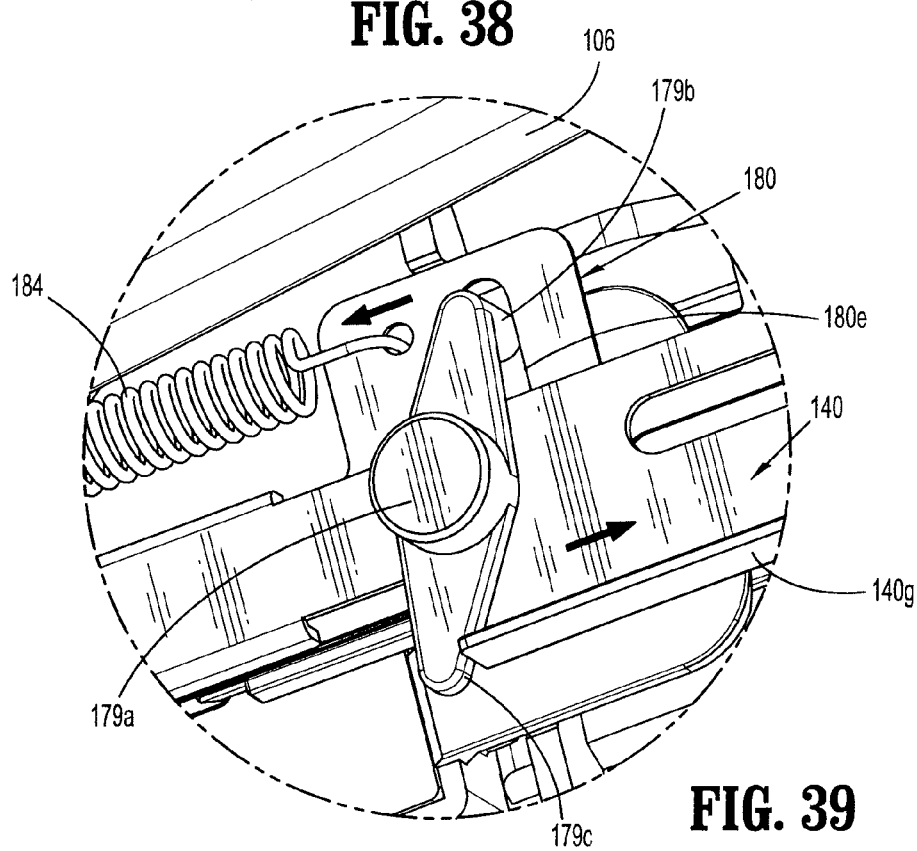
FIG. 39 is an enlarged view of the indicated area of detail of FIG. 26, during an opening of the handles.

As seen in FIG. 39, as drive channel 140 is moved proximally, flange or wall 140g of drive channel 140 disengages from against cam surface 179c of pivot arm 179 allowing for biasing member 184 to constrict and move wedge plate 180 in a distal direction. As wedge plate 180 is moved in a distal direction, distal end 180a of wedge plate 180 is reinserted or reintroduced into jaws 120, thereby spreading jaws 120 apart, as seen in FIG. 43.

As seen in FIGS. 40 and 41, as wedge plate 180 is moved distally, proximal tab 176 of clip follower 174 engages in a window 180b of wedge plate 180 and is thus urged distally a given distance. As clip follower 174 is urged distally, stack of clips "C" are also urged distally. As seen in FIG. 41, when wedge plate 180 reaches a distal-most position, clip channel 170 abuts, engages, urges or otherwise cams against proximal portion 175b of distal tab 175 until web 180f of wedge plate 180 rests substantially beneath distal portion 175a of distal tab 175. In so doing, proximal portion 175b of distal tab 175 is moved to extend into an incrementally more distal window 172 of clip channel 170.

Figure 42:
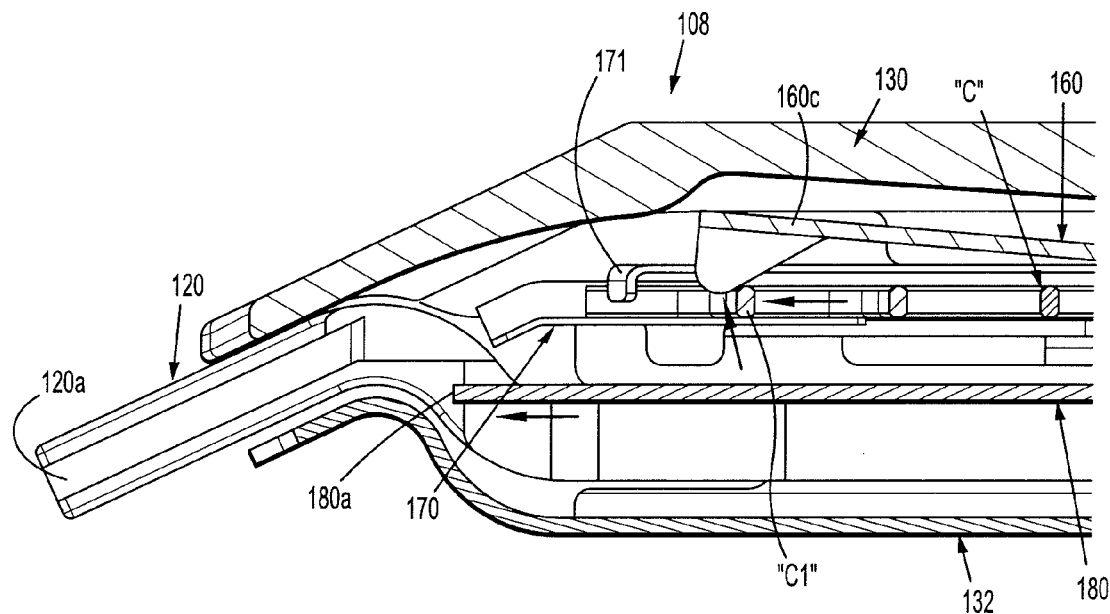
FIGS. 42 and 43 are enlarged views of the indicated area of detail 8 of FIG. 5, during the opening of the handles.
Figure 43:
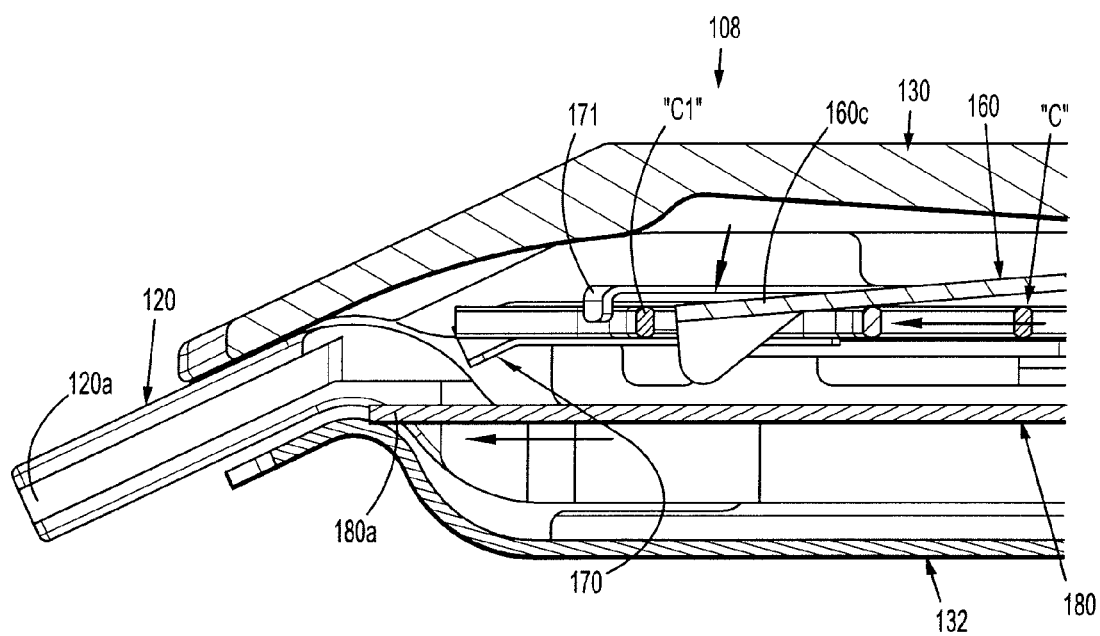

As seen in FIGS. 42 and 43, as clip follower 174 is urged forward, moving the stack of clips "C" forward, a distal-most clip "C1" moves distal of pusher 160c by camming beneath pusher 160c of pusher bar 160 until distal-most clip "C1" is caught by tangs 171 of clip applier 170.

Figure 38:
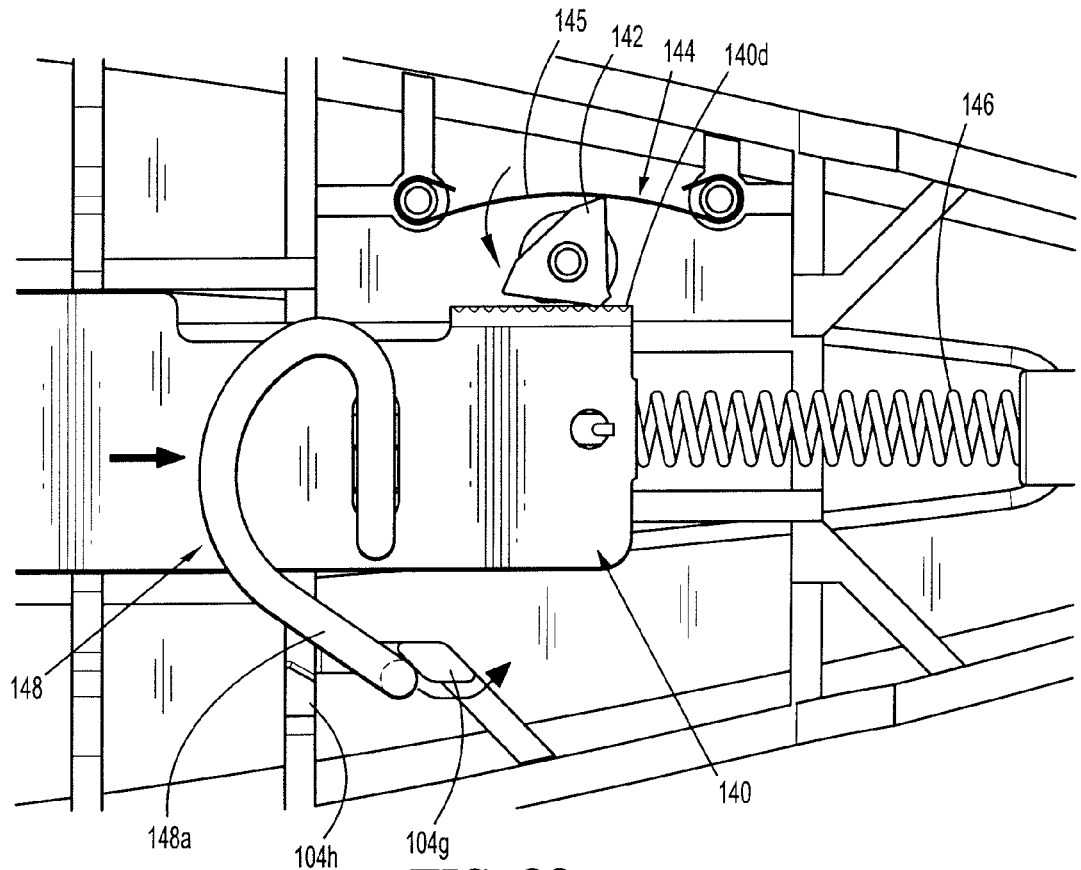
FIG. 38 is an enlarged, plan view of the rack and pawl assembly of the clip applier of FIGS. 1-37, during an opening of the handles.

Turning momentarily to FIG. 38, as drive channel 140 is moved in a proximal direction, arm 148a of audible/tactile indicator 148 snaps back over ledge 104g and re-sets itself for the next firing stroke or squeeze of handles 106.

As mentioned above, as drive channel 140 is moved in a proximal direction, drive pin 124 moved counter actuator 196 in a proximal direction, out of engagement with contact 194a of processor 194.

Figure 44:
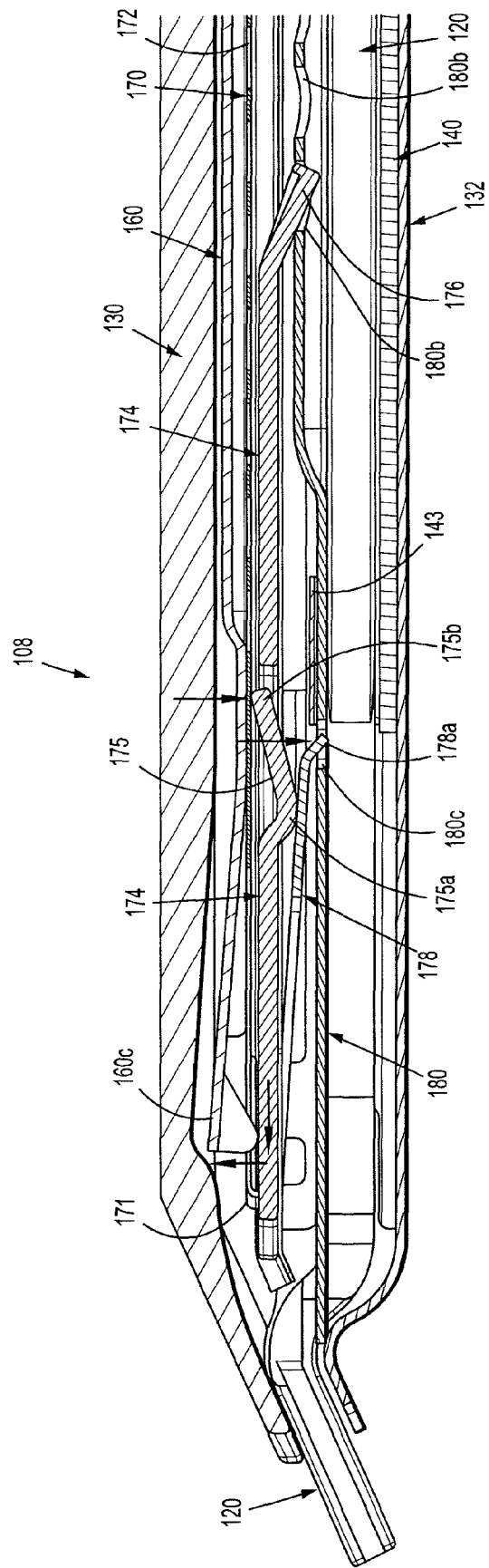
FIG. 44 is an enlarged view of the indicated area of detail 8 of FIG. 5, after a final clip has been expelled from the clip applier.

Turning now to FIG. 44, a distal end of clip applier 100 is illustrated following a complete stroke or squeezing of handles 106 and after a final clip has been expelled therefrom. Following firing of the last clip, as seen in FIG. 44, proximal tab 176 of clip follower is disposed within a distal-most aperture or window of apertures 180b of wedge plate 180. In this manner, as wedge plate 180 is moved distally following a firing of a clip, in the manner described above, clip follower 174 is also moved distally. However, in the present arrangement, as clip follower 174 is moved distally, distal tab 175 thereof is moved distal of a distal-most window of windows 172 of clip carrier 170. In this manner, proximal portion 175b of distal tab 175 engages against an inner surface of a top wall of clip carrier 170 and is cammed or urged downwardly.

As proximal portion 175b of distal tab 175 is cammed or urged downwardly, distal portion 175a of distal tab 175 engages against an upper surface of tab 178a of lockout 178 and cams or urges tab 178a of lockout 178 downwardly, across a path of strap 143, supported on drive channel 140, and into distal window 180c of wedge plate 180. In this manner, if drive channel 140 is advanced distally, in the manner described above, strap 143 will abut against tab 178a of lockout 178 and prevent or block strap 143 and, in turn, drive channel 140 from moving distally. At this stage, pawl 142 is located in a dwell, distal of rack 140d, and handles 106 are arranged in a fully opened position and are thus not capable of being opened any further. In this configuration, clip applier is locked out and can no longer be used.

Figure 45:
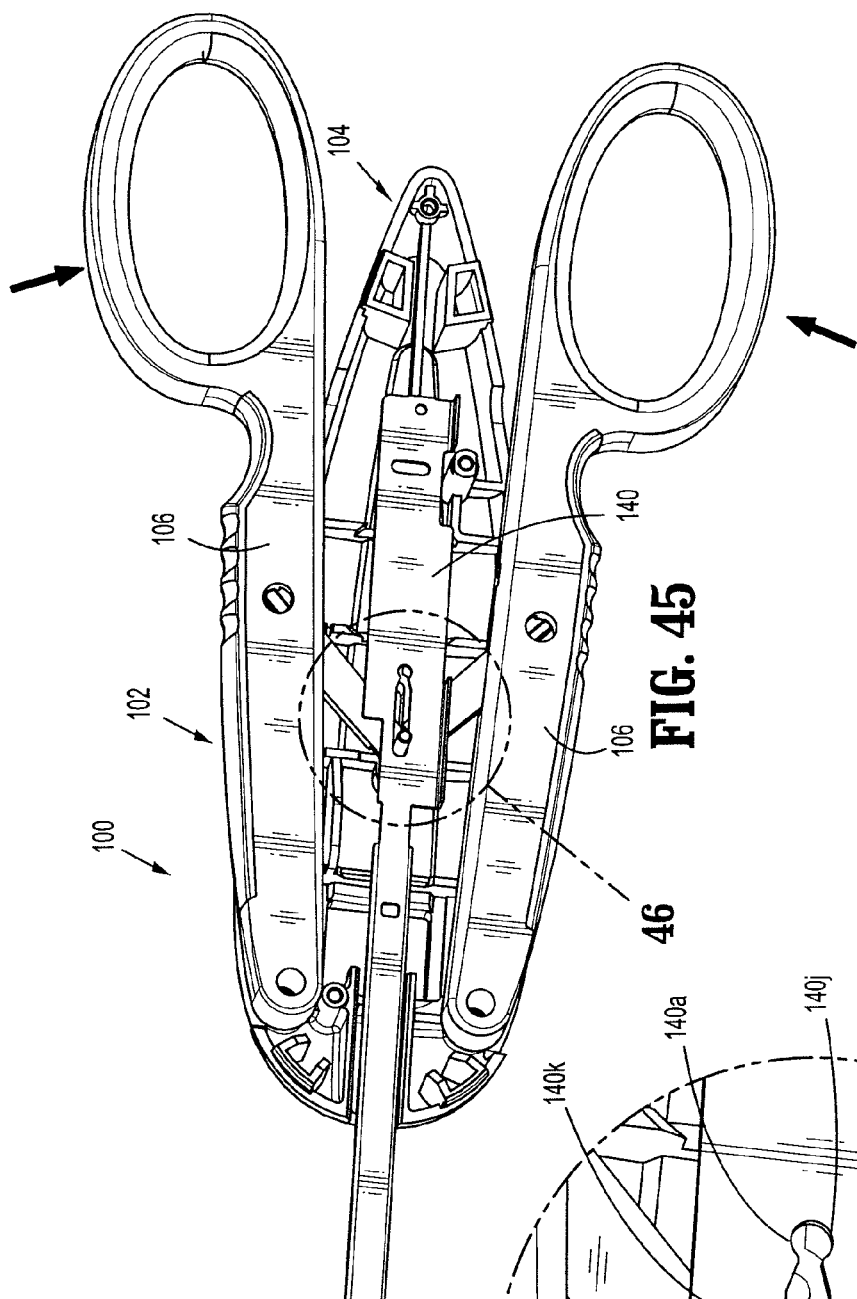
FIG. 45 is a bottom, perspective view of the clip applier of FIGS. 1-24, with the lower housing half removed therefrom, illustrating the handles of the clip applier being squeezed after the final clip has been expelled therefrom.
Figure 46:
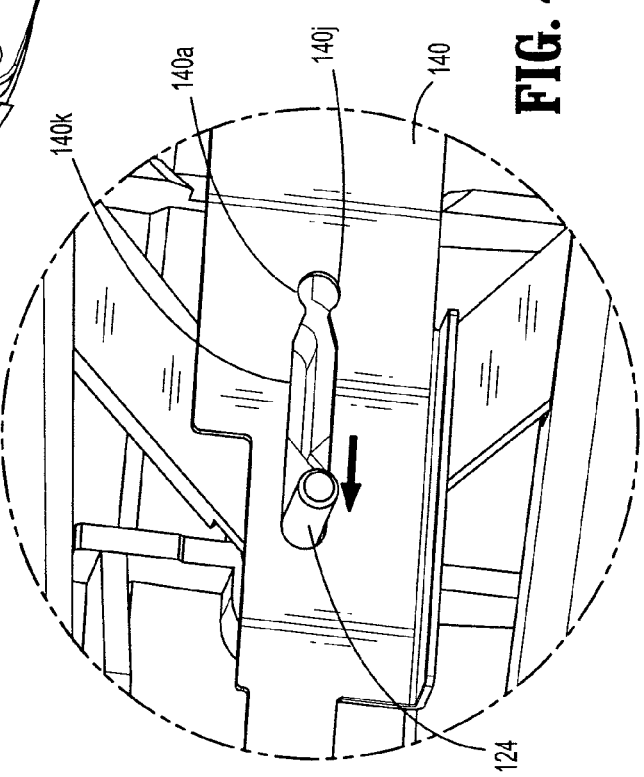
FIG. 46 is an enlarged view of the indicated area of detail of FIG. 45.

As seen in FIGS. 45 and 46, if a surgeon tries to break through the locked out configuration of clip applier 100 by exerting an excessive force (i.e., a force greater than a predetermined limit) on handles 106 thereof, drive pin 124 will be urged beyond a lip 140*j* defining pivot point 140*a* of drive channel 140 and into an elongate slot 140*k*. Elongate slot 140*k* will have a length sufficient to accommodate substantially all of a distance of travel of drive pin 124.

Figure 47:
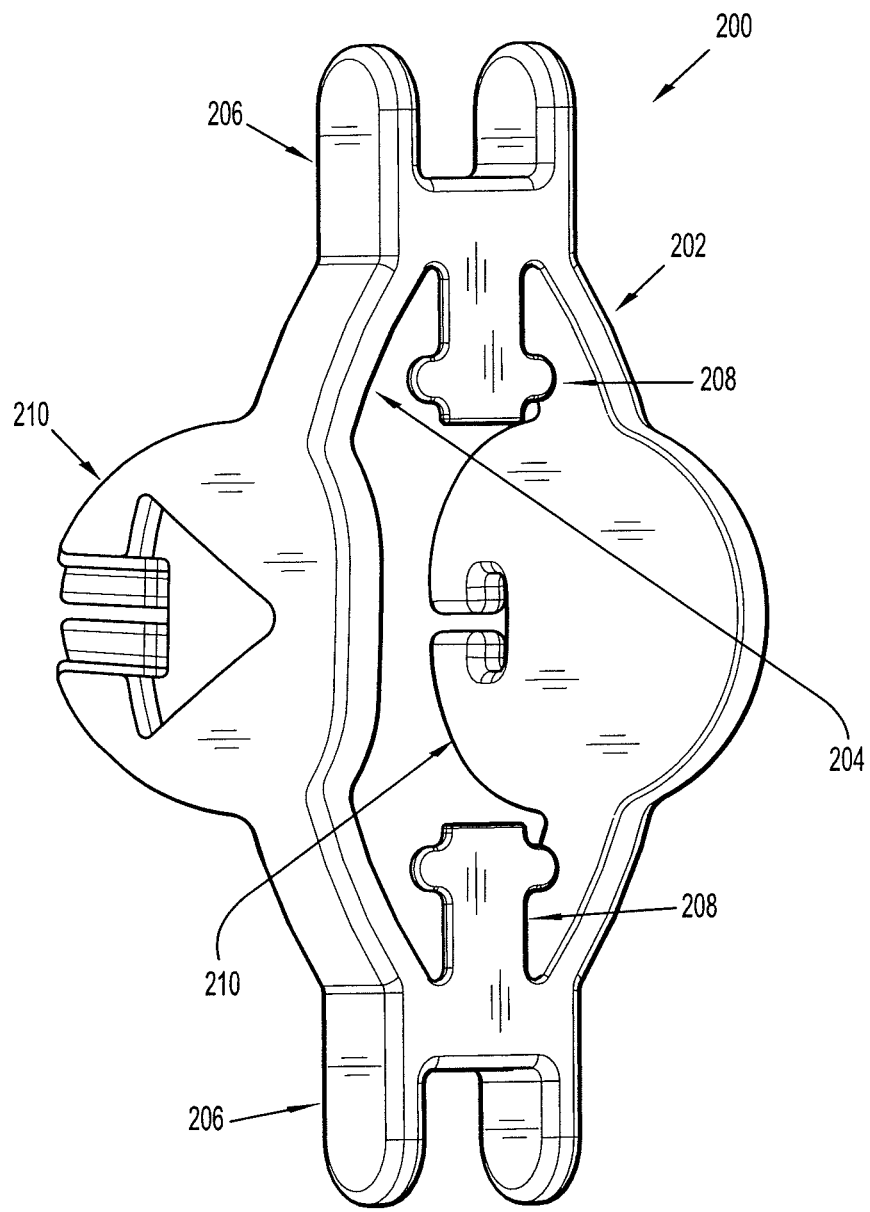
FIG. 47 is a rear, perspective view of a shipping wedge, according to an embodiment of the present disclosure, for use with the clip applier of FIGS. 1-46.
Figure 48:
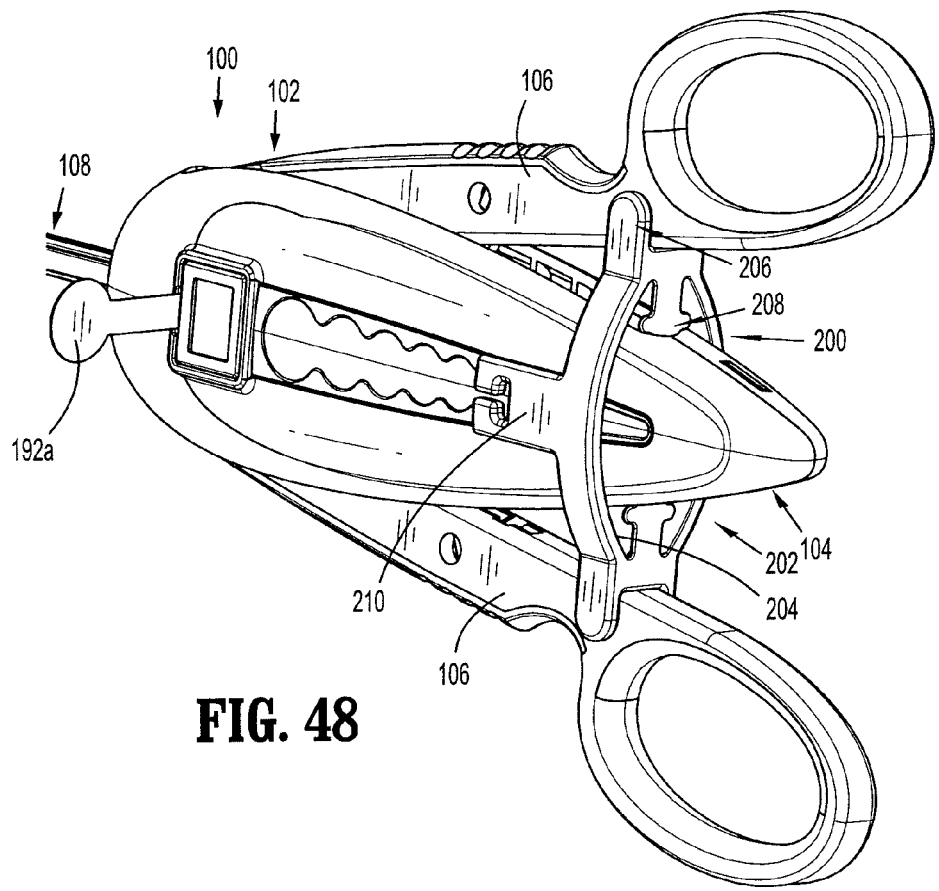
FIG. 48 is a perspective view of the clip applier of FIGS. 1-46, illustrating the shipping wedge of FIG. 47 operatively secured thereto.
Figure 49:
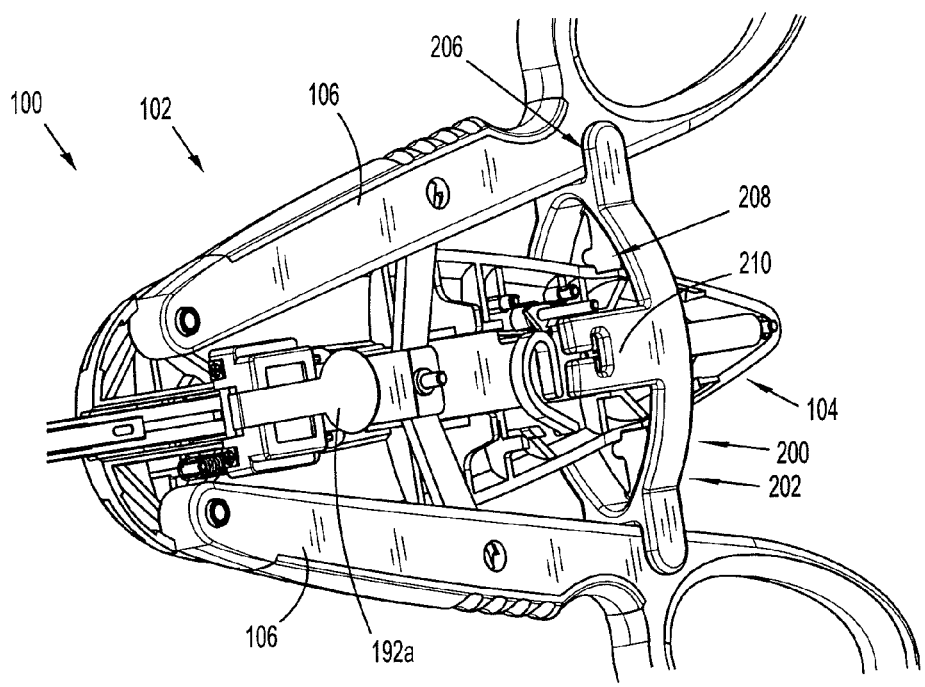
FIG. 49 is a further perspective view of the clip applier of FIG. 48, having a housing half removed therefrom, illustrating the shipping wedge secured thereto.

Turning now to FIGS. 47-49, clip applier 100 may include a shipping wedge 200 supported on housing 104 and interposed between handles 106. Shipping wedge 200 functions to maintain handles 106 spaced apart or un-squeezed during a shipment and/or storage of clip applier 100. In one embodiment, tab 192*a* of counter mechanism 190 is connected to shipping wedge 200 such that removal of shipping wedge 200 from clip applier 100 results in the removal of tab 192*a*, as described above.

As seen in FIGS. 47-49, shipping wedge 200 includes a body portion 202 in the form of a collar, defining a passage 204 configured and dimensioned for receipt of a portion of housing 104 therein. Shipping wedge 200 includes uprights 206 extending outwardly from opposed sides of body portion 202 and being configured to receive handles 106 therein. Shipping wedge 200 further includes tabs 208 extending inwardly from opposed sides of body portion 202 and being substantially aligned with uprights 206. Tabs 208 of shipping wedge 200 are configured and dimensioned to engage against an outer surface of housing 104 when shipping wedge 200 is properly secured to clip applier 100.

Shipping wedge 200 includes securement members 210 extending therefrom for engaging housing 104 and maintaining shipping wedge 200 in position relative to clip applier 100. Securement members 210 may be configured and adapted for snap-fit engagement with housing 104 or for snap-fit engagement with complementary structure provided on housing 104.

Figure 50:
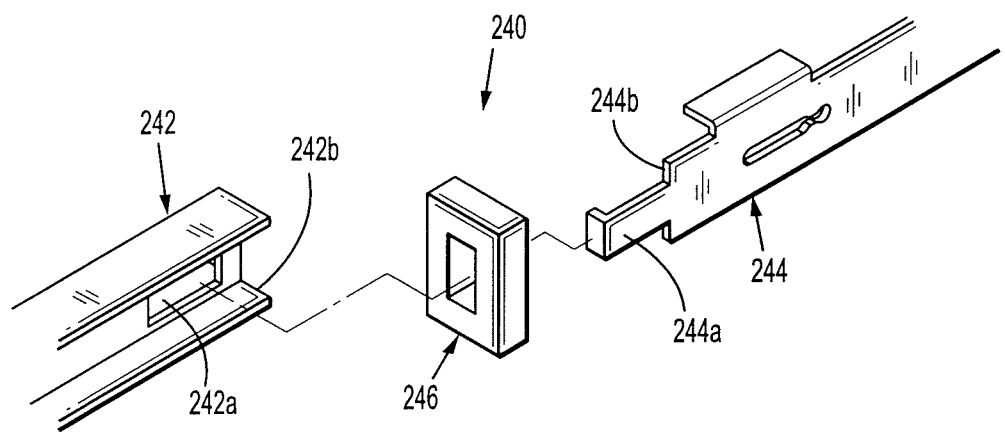
FIG. 50 is an exploded, perspective view of a drive channel for use with the clip applier of FIGS. 1-49, according to another embodiment of the present disclosure.
Figure 51:
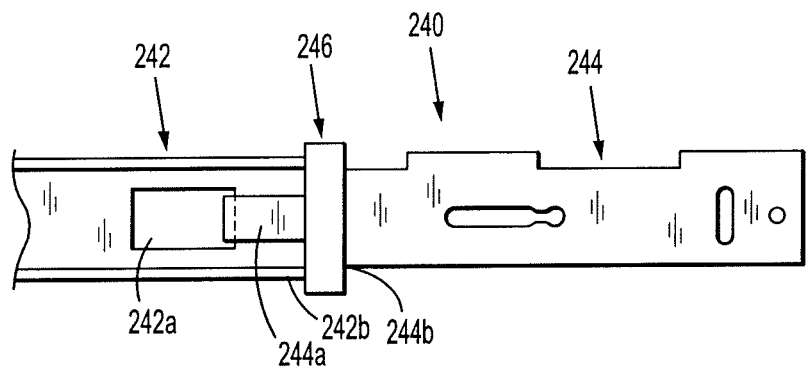
FIG. 51 is a plan view of the drive channel of FIG. 50, shown in an assembled and operative condition.

Turning now to FIGS. 50 and 51, a drive channel for use with clip applier 100, according to another embodiment of the present disclosure, is generally designated as 240. Drive channel 240 functions to accommodate for the situation where a second clip is being applied over an existing clip, previously applied, or where a clip is being applied over a hard/dense material, such as bone. In the even that a clip is being applied over an existing clip or over a hard material, it is desirable for the clip applier and, in particular, the drive channel to complete is forward or distal stroke in order for the rack of the ratchet mechanism to clear the pawl and allow for the drive channel to return to a proximal-most position.

Accordingly, as seen in FIGS. 50 and 51, drive channel 240 includes a distal drive channel 242 and a proximal drive channel 244 axially, slidably associated with one another. Distal drive channel 242 defines a window 242*a* formed in a backspan thereof for engaging and receiving a tab 244*a* extending distally from proximal drive channel 244. Drive channel 240 includes a compression member 246 interposed between distal drive channel 242 and proximal drive channel 244. In particular, compression member 246 is supported on tab 244*a* of proximal drive channel 244 and is engageable with a proximal surface 242*b* of distal drive channel 242 and a distal surface 244*b* of proximal drive channel 244. Compression member 246 may be constructed of rubber and has a given or know durometer and a given, un-compressed width.

In use, as drive channel 240 is moved in a distal direction, proximal drive channel 244 engages/presses against compression member 246 and, in turn, distal drive channel 242. The material of construction of compression member 246 is selected such that substantially little to no compression of the width of compression member 246 is exhibited during firing of clip applier 100 to apply a clip to body tissue. However, if a clip is being applied over another clip or over a hard material, distal movement of distal drive channel 242 is blocked. Since the rack of the ratchet mechanism has engaged the pawl, proximal drive channel 244 can not return to a proximal-most position until it completes its distal stroke. Accordingly, in order to return proximal drive channel 244 to the home or proximal-most position, handles 106 are squeezed further, forcing proximal drive channel 244 into compression member 246, causing compression member 246 to compress an amount sufficient for the rack of the ratchet mechanism to clear and disengage the pawl, thereby allowing for the proximal drive channel 244 to return to the home or proximal-most position.

As proximal drive channel 244 is returning to the home or proximal-most position, tab 244*a* of proximal drive channel 244 engages distal drive channel 242 and pulls distal drive channel 242 in a proximal direction.

Figure 52:
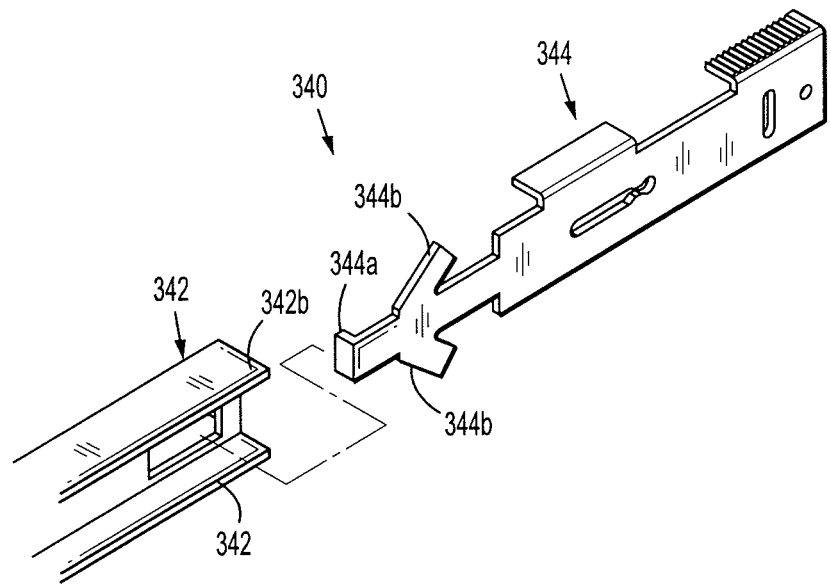
FIG. 52 is an exploded, perspective view of a drive channel for use with the clip applier of FIGS. 1-49, according to yet another embodiment of the present disclosure.
Figure 53:
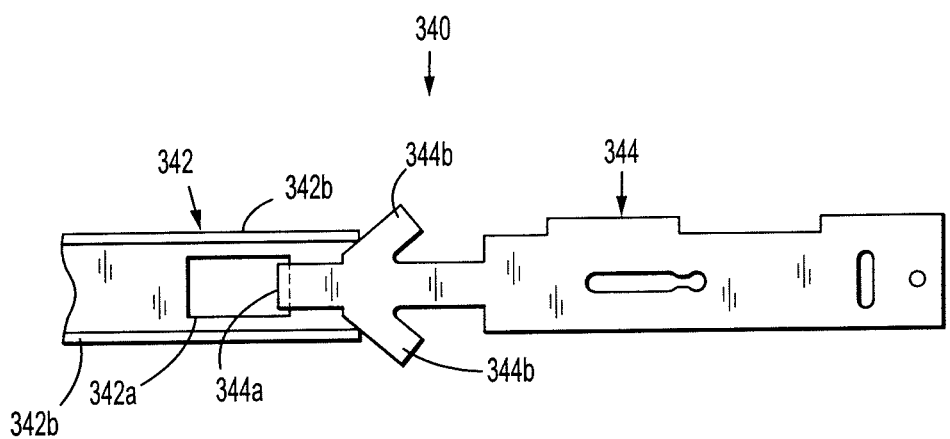
FIG. 53 is a plan view of the drive channel of FIG. 52, shown in an assembled and operative condition.

Turning now to FIGS. 52 and 53, a drive channel according to another embodiment of the present disclosure is shown generally as 340. Drive channel 340 is substantially similar to drive channel 240 and thus will only be discussed in detail herein to the extent necessary to identify differences in construction and operation.

As seen in FIGS. 52 and 53, tab 344*a* of distal drive channel 344 a pair of arms 344*b* extending from opposite sides thereof. Distal drive channel 342 includes a pair of spaced apart, opposed side walls 342*b*. Arms 344*b* are angled with respect to a longitudinal axis of drive channel 340 in a substantially proximal direction. Arms 344*b* of proximal drive channel 344 have an un-deflected condition wherein arms 344*b* extend beyond side walls 342*b* of distal drive channel 342. Arms 344*b* of proximal drive channel 344 have a deflected condition wherein arms 344*b* are flexed between side walls 342*b* of distal drive channel 342.

In use, as drive channel 340 is moved in a distal direction, arms 344*b* of proximal drive channel 344 engage/press against side walls 342*b* of distal drive channel 342. The dimensions and material of construction of arms 344*b* of proximal drive channel 342 are selected such that substantially little to no deflection of arms 344*b* is exhibited during firing of clip applier 100 to apply a clip to body tissue. However, if a clip is being applied over another clip or over a hard material, distal movement of distal drive channel 342 is blocked. Since the rack of the ratchet mechanism has engaged the pawl, proximal drive channel 344 can not return to a proximal-most position until it completes its distal stroke. Accordingly, in order to return proximal drive channel 344 to the home or proximal-most position, handles 106 are squeezed further, forcing proximal drive channel 344 distally, thereby causing arms 344*b* thereof to be cammed and be deflected by side walls 342*b* of distal drive channel 342, causing proximal drive channel 344 to move distally an amount sufficient for the rack of the ratchet mechanism to clear and disengage the pawl, thereby allowing for the proximal drive channel 344 to return to the home or proximal-most position.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:
   a housing;
   a pair of handles pivotably connected to opposite sides of the housing;
   a channel assembly fixed to and extending from the housing;
   a jaw assembly including a pair of jaws extending from an end of said channel assembly, opposite said housing, said jaw assembly adapted to accommodate a clip therein and being operable to effect closure of a clip in response to movement of said handles;
   a clip carrier disposed within said channel assembly and defining a channel and a plurality of windows;
   a wedge plate slidably disposed within said channel assembly, said wedge plate being operatively connected to said handles and including a plurality of apertures formed along a length thereof;
   a clip pusher bar slidably positioned within at least one of said housing and said channel assembly, said pusher bar having a first end operatively connected to at least one of said handles and a second end defining a pusher terminating proximate said pair of jaws;
   a drive channel slidably disposed within at least one of said housing and said channel assembly, said drive channel having a first end operatively connected to at least one of said handles and a second end configured and dimensioned to selectively engage said pair of jaws to effectuate closure of said pair of jaws;
   a plurality of clips slidably disposed within said channel of said clip carrier;
   a clip follower slidably disposed within said channel of said clip carrier at a location proximal of said plurality of clips, said clip follower being configured and adapted for selective engagement with said windows of said clip carrier and said apertures of said wedge plate, wherein said clip follower is configured and adapted to distally urge said plurality of clips relative to said clip carrier upon a distal advancement of said wedge plate; and
   a pusher bar cam pivotably supported on the drive channel and movable therewith, said pusher bar cam extending through a slot formed in said wedge plate and into a window formed in said pusher bar, wherein as said drive channel is moved distally said pusher bar cam moves said pusher bar distally.

2. The clip applier according to claim 1, wherein said pusher bar is moved towards said jaws as said handles are approximated in a first direction an initial amount to move said distal-most clip between said jaws, and said pusher bar is configured and adapted to move towards said housing as said handles are approximated an additional amount in said first direction to move said pusher behind a distal-most clip in said plurality of clips.

3. The clip applier according to claim 2, wherein said drive channel is moved towards said jaw assembly as said handles are moved in said first direction to move said distal end thereof against said jaws to close said jaws, and wherein said drive channel is moved away from said jaws as said handles are moved in a second direction to move said distal end thereof away from said jaws to allow said jaws to open.

4. The clip applier according to claim 1, further comprising a pivot arm operatively connected to said wedge plate and selectively engageable by said drive channel, wherein rotation of said pivot arm, during distal movement of said drive channel, results in proximal movement of said wedge plate.

5. The clip applier according to claim 1, wherein during distal movement of said drive channel, said pusher bar cam is rotated relative thereto such that said pusher bar cam disengages from said window of said pusher bar allowing said pusher bar to move proximally.

6. The clip applier according to claim 1, wherein said wedge plate is biased to a distal position.

7. The clip applier according to claim 1, wherein at least one of said pusher bar and said drive channel is biased to a proximal position.

8. The clip applier according to claim 1, further comprising a ratchet mechanism including:
   a rack, having a plurality of ratchet teeth, associated with said drive channel; and
   a pawl, having at least one tooth, disposed at a location to selectively engage said rack, wherein said pawl is biased into engagement with said rack, wherein as said drive channel is longitudinally reciprocated, said plurality of teeth are passed over said pawl, and wherein said pawl prevents inadvertent return of said drive channel before full actuation of said handles.

9. The clip applier according to claim 1, further comprising a lockout disposed in a distal end of said channel assembly, wherein said lockout is actuated by said clip follower when a last clip is expelled from said clip applier.

10. The clip applier according to claim 9, wherein said lockout is urged by said clip follower to extend across a path of said drive channel, thereby preventing said drive channel from moving distally.

11. The clip applier according to claim 3, further comprising a drive pin operatively received in a pivot point formed in said drive channel to transmit axial forces to said drive channel during movement of said handles, wherein said pivot point is separated from an elongate slot by at least one lip.

12. The clip applier according to claim 1, further comprising a shipping wedge selectively attachable to said housing and being configured and adapted to engage each of said handles.

13. The clip applier according to claim 1, further comprising a counter mechanism supported in at least one of said housing and said channel assembly, wherein said counter mechanism is configured and adapted to display a change in said clip applier upon each actuation of said handles.

14. The clip applier according to claim 1, wherein said drive channel is configured and dimensioned to at least partially surround said jaws and said wedge plate, wherein said drive channel includes a strap extending across a distal end thereof for maintaining said jaws and said wedge plate within said drive channel.

15. A surgical clip applier, comprising:
   a housing;
   a pair of handles pivotably connected to opposite sides of the housing;
   a channel assembly fixed to and extending from the housing;
   a clip carrier disposed within said channel assembly and defining a channel;
   a drive channel slidably disposed within at least one of said housing and said channel assembly, said drive channel having a first end operatively connected to at least one of said handles and a second end configured and dimensioned to selectively engage a pair of jaws to effectuate closure of said pair of jaws;

a plurality of clips slidably disposed within said channel of said clip carrier;

a clip follower slidably disposed within said channel of said clip carrier at a location proximal of said plurality of clips; and a lockout disposed in a distal end of said channel assembly, wherein said lockout is actuated by said clip follower when a last clip is expelled from said clip applier, wherein a tab of said clip follower engages against said lockout to urge said lockout to extend across a path of said drive channel, thereby preventing said drive channel from moving distally.

16. The clip applier according to claim 15, further comprising a wedge plate slidably disposed within said channel assembly, said wedge plate being operatively connected to said handles and including a plurality of apertures formed along a length thereof; wherein said clip carrier defines a plurality of windows; and wherein said clip follower is configured and adapted for selective engagement with said windows of said clip carrier and said apertures of said wedge plate, wherein said clip follower is configured and adapted to distally urge said plurality of clips relative to said clip carrier upon a distal advancement of said wedge plate.

17. The clip applier according to claim 16, further comprising a jaw assembly including a pair of jaws extending from an end of said channel assembly, opposite said housing, said jaw assembly being adapted to accommodate a clip therein and being operable to effect closure of a clip in response to movement of said handles.

18. The clip applier according to claim 17, further comprising a clip pusher bar slidably positioned within at least one of said housing and said channel assembly, said pusher bar having a first end operatively connected to at least one of said handles and a second end defining a pusher terminating proximate said pair of jaws, said pusher bar being moved towards said jaws as said handles are approximated in a first direction an initial amount to move said distal-most clip between said jaws, and said pusher bar being configured and adapted to move towards said housing as said handles are approximated an additional amount in said first direction to move said pusher behind a distal-most clip in said plurality of clips.

19. The clip applier according to claim 18, further comprising a pusher bar cam pivotably supported on the drive channel and movable therewith, said pusher bar cam extending through a slot formed in said wedge plate and into a window formed in said pusher bar, wherein as said drive channel is moved distally said pusher bar cam moves said pusher bar distally.

20. The clip applier according to claim 19, wherein during distal movement of said drive channel, said pusher bar cam is rotated relative thereto such that said pusher bar cam disengages from said window of said pusher bar allowing said pusher bar to move proximally.

21. The clip applier according to claim 16, further comprising a pivot arm operatively connected to said wedge plate and selectively engageable by said drive channel, wherein rotation of said pivot arm, during distal movement of said drive channel, results in proximal movement of said wedge plate.

22. The clip applier according to claim 15, further comprising a ratchet mechanism including:

a rack, having a plurality of ratchet teeth, associated with said drive channel; and a pawl, having at least one tooth, disposed at a location to selectively engage said rack, wherein said pawl is biased into engagement with said rack, wherein as said drive channel is longitudinally reciprocated, said plurality of teeth are passed over said pawl, and wherein said pawl prevents inadvertent return of said drive channel before full actuation of said handles.

23. The clip applier according to claim 15, further comprising a drive pin operatively received in a pivot point formed in said drive channel to transmit axial forces to said drive channel during movement of said handles, wherein said pivot point is separated from an elongate slot by at least one lip.

24. The clip applier according to claim 17, wherein said drive channel is configured and dimensioned to at least partially surround said jaws and said wedge plate, wherein said drive channel includes a strap extending across a distal end thereof for maintaining said jaws and said wedge plate within said drive channel.

* * * * *